(12) United States Patent
McLean et al.

(10) Patent No.: US 9,149,302 B2
(45) Date of Patent: Oct. 6, 2015

(54) APPARATUS AND DEVICES FOR PERCUTANEOUSLY EXTENDING AN EXISTING SPINAL CONSTRUCT

(71) Applicant: SPINE WAVE, INC., Shelton, CT (US)

(72) Inventors: Scott McLean, Waterbury, CT (US); Tim E. Adamson, Charlotte, NC (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 14/013,234

(22) Filed: Aug. 29, 2013

(65) Prior Publication Data

US 2014/0066988 A1 Mar. 6, 2014

Related U.S. Application Data

(62) Division of application No. 13/617,312, filed on Sep. 14, 2012, now Pat. No. 8,523,906.

(60) Provisional application No. 61/568,199, filed on Dec. 8, 2011.

(51) Int. Cl.
*A61B 17/70* (2006.01)
*A61B 17/88* (2006.01)

(52) U.S. Cl.
CPC .......... *A61B 17/7052* (2013.01); *A61B 17/705* (2013.01); *A61B 17/708* (2013.01); *A61B 17/7011* (2013.01); *A61B 17/7032* (2013.01); *A61B 17/7037* (2013.01);
(Continued)

(58) Field of Classification Search
CPC .......... A61B 17/7047; A61B 17/7049; A61B 17/705; A61B 17/7052

USPC .......... 606/86 A, 96–99, 104, 246–279, 914, 606/916
See application file for complete search history.

(56) References Cited

U.S. PATENT DOCUMENTS 427,642 A   5/1890 Wack
4,097,015 A   6/1978 Frishman
(Continued)

FOREIGN PATENT DOCUMENTS

DE   9402695   5/1994
EP   0811357 A1   12/1997

OTHER PUBLICATIONS

Johnson & Johnson Company; DePuySpine™, Surgical Technique, VIPER™, 3D MIS Correction Set; Pelvic Fixation; (2011).

*Primary Examiner* — Jerry Cumberledge
(74) *Attorney, Agent, or Firm* — Hoffmann & Baron, LLP

(57) ABSTRACT

Apparatus and devices for percutaneously extending an existing spinal construct ipsilaterally with an additional spinal construct in a patient are disclosed. The additional spinal construct comprises a rod connector that includes an elongate additional rod integrally attached thereto. The additional rod is placed through an access port in a first orientation generally parallel to the longitudinal axis of the access port and rotated to a different second orientation generally transverse to the longitudinal axis of the access port. During such rotation the additional rod is moved subcutaneously beneath the skin of the patient from the existing spinal rod to an additional bone engaging implant. In another arrangement, the extension of an existing spinal construct in a minimally invasive procedure comprises a rod connector having an offset support for receiving an additional spinal rod that may be placed laterally interiorly or exteriorly of the existing spinal construct.

15 Claims, 32 Drawing Sheets

(52) U.S. Cl.
CPC ........ *A61B 17/7055* (2013.01); *A61B 17/7085* (2013.01); *A61B 17/7091* (2013.01); *A61B 17/88* (2013.01)

(56) References Cited

U.S. PATENT DOCUMENTS

| | | | |
|---|---|---|---|
| 4,611,582 A | 9/1986 | Duff | |
| 5,261,913 A | 11/1993 | Marnay | |
| 5,306,275 A | 4/1994 | Bryan | |
| 5,330,473 A | 7/1994 | Howland | |
| 5,334,203 A | 8/1994 | Wagner | |
| 5,487,742 A | 1/1996 | Cotrel | |
| 5,520,688 A | 5/1996 | Lin | |
| 5,534,001 A | 7/1996 | Schlapfer et al. | |
| 5,542,946 A | 8/1996 | Logroscino et al. | |
| 5,569,246 A | 10/1996 | Ojima et al. | |
| 5,609,593 A | 3/1997 | Errico et al. | |
| 5,624,442 A | 4/1997 | Mellinger et al. | |
| 5,630,816 A | 5/1997 | Kambin | |
| 5,651,789 A | 7/1997 | Cotrel | |
| 5,688,273 A | 11/1997 | Errico et al. | |
| 5,688,274 A | 11/1997 | Errico et al. | |
| 5,716,355 A | 2/1998 | Jackson et al. | |
| 5,752,957 A | 5/1998 | Ralph et al. | |
| 5,984,923 A | 11/1999 | Breard | |
| 5,989,251 A | 11/1999 | Nichols | |
| 6,015,409 A | 1/2000 | Jackson | |
| 6,027,533 A | 2/2000 | Olerud | |
| 6,171,311 B1 | 1/2001 | Richelsoph | |
| 6,187,000 B1 | 2/2001 | Davison et al. | |
| 6,187,005 B1 | 2/2001 | Brace et al. | |
| 6,273,914 B1 | 8/2001 | Papas | |
| 6,302,882 B1 | 10/2001 | Lin et al. | |
| 6,352,537 B1* | 3/2002 | Strnad | 606/276 |
| 6,368,320 B1 | 4/2002 | Le Couedic et al. | |
| 6,379,354 B1 | 4/2002 | Rogozinski | |
| 6,488,682 B2 | 12/2002 | Kikuchi et al. | |
| 6,494,411 B1 | 12/2002 | Bjorklund | |
| 6,530,929 B1 | 3/2003 | Justis et al. | |
| 6,592,590 B2 | 7/2003 | Simon | |
| 6,626,904 B1 | 9/2003 | Jammet et al. | |
| 6,682,529 B2 | 1/2004 | Stahurski | |
| 6,716,213 B2 | 4/2004 | Shitoto | |
| 6,752,807 B2 | 6/2004 | Lin et al. | |
| 6,783,526 B1 | 8/2004 | Lin et al. | |
| 6,802,844 B2 | 10/2004 | Ferree | |
| 6,911,030 B1 | 6/2005 | Vanacker et al. | |
| D537,940 S | 3/2007 | Buttler | |
| 7,207,992 B2 | 4/2007 | Ritland | |
| 7,250,052 B2 | 7/2007 | Landry et al. | |
| 7,306,603 B2 | 12/2007 | Boehm, Jr. et al. | |
| 7,465,306 B2 | 12/2008 | Pond, Jr. et al. | |
| 7,476,240 B2 | 1/2009 | Raymond et al. | |
| 7,527,638 B2 | 5/2009 | Anderson et al. | |
| 7,572,276 B2 | 8/2009 | Lim et al. | |
| 7,588,588 B2 | 9/2009 | Spitler et al. | |
| 7,618,442 B2 | 11/2009 | Spitler et al. | |
| 7,648,521 B2 | 1/2010 | Hestad | |
| 7,678,112 B2 | 3/2010 | Rezach | |
| 7,695,499 B2 | 4/2010 | Morrison et al. | |
| 7,708,763 B2 | 5/2010 | Selover et al. | |
| 7,736,370 B2 | 6/2010 | Sweeney | |
| 7,799,036 B2 | 9/2010 | Davison et al. | |
| 7,824,410 B2 | 11/2010 | Simonson et al. | |
| 7,833,248 B2* | 11/2010 | Markworth et al. | 606/253 |
| 7,905,907 B2 | 3/2011 | Spitler et al. | |
| 7,922,746 B2 | 4/2011 | Miller | |
| 7,931,673 B2 | 4/2011 | Hestad et al. | |
| 7,976,567 B2 | 7/2011 | Null et al. | |
| 8,007,522 B2 | 8/2011 | Hutchinson | |
| 8,012,184 B2 | 9/2011 | Schlapfer et al. | |
| 8,021,399 B2 | 9/2011 | Ritland | |
| 8,038,699 B2 | 10/2011 | Cohen et al. | |
| 8,043,343 B2 | 10/2011 | Miller et al. | |
| 8,080,015 B2 | 12/2011 | Buttler et al. | |
| 8,092,498 B2 | 1/2012 | Samudrala et al. | |
| 8,092,504 B2 | 1/2012 | Warnick | |
| 8,097,022 B2 | 1/2012 | Marik | |
| 8,105,361 B2 | 1/2012 | Anderson et al. | |
| 8,262,701 B2* | 9/2012 | Rathbun et al. | 606/250 |
| 8,864,799 B2* | 10/2014 | Kraus | 606/253 |
| 2003/0004512 A1 | 1/2003 | Farris et al. | |
| 2003/0083659 A1 | 5/2003 | Lin et al. | |
| 2003/0093078 A1 | 5/2003 | Ritland | |
| 2003/0130659 A1 | 7/2003 | Haider | |
| 2003/0208203 A1 | 11/2003 | Lim et al. | |
| 2004/0143265 A1 | 7/2004 | Landry et al. | |
| 2005/0080320 A1 | 4/2005 | Lee et al. | |
| 2005/0080417 A1 | 4/2005 | Alexis et al. | |
| 2005/0090821 A1* | 4/2005 | Berrevoets et al. | 606/61 |
| 2005/0090824 A1 | 4/2005 | Shluzas et al. | |
| 2005/0107789 A1 | 5/2005 | Sweeney | |
| 2005/0228378 A1 | 10/2005 | Kalfas et al. | |
| 2005/0240265 A1 | 10/2005 | Kuiper et al. | |
| 2006/0079892 A1 | 4/2006 | Roychowdhury et al. | |
| 2006/0142758 A1 | 6/2006 | Petit | |
| 2006/0276794 A1 | 12/2006 | Stern | |
| 2007/0016189 A1 | 1/2007 | Lake et al. | |
| 2007/0043357 A1* | 2/2007 | Kirschman | 606/61 |
| 2007/0043365 A1* | 2/2007 | Ritland | 606/61 |
| 2007/0055242 A1 | 3/2007 | Bailly | |
| 2007/0078460 A1 | 4/2007 | Frigg et al. | |
| 2007/0083201 A1 | 4/2007 | Jones et al. | |
| 2007/0088359 A1 | 4/2007 | Woods et al. | |
| 2007/0093827 A1 | 4/2007 | Warnick | |
| 2007/0123862 A1 | 5/2007 | Warnick | |
| 2007/0123867 A1 | 5/2007 | Kirschman | |
| 2007/0135817 A1 | 6/2007 | Ensign | |
| 2007/0198014 A1 | 8/2007 | Graf et al. | |
| 2007/0233091 A1 | 10/2007 | Naifeh et al. | |
| 2007/0250061 A1 | 10/2007 | Chin et al. | |
| 2007/0270805 A1 | 11/2007 | Miller et al. | |
| 2007/0270816 A1 | 11/2007 | Rezach | |
| 2007/0270817 A1 | 11/2007 | Rezach | |
| 2007/0276384 A1 | 11/2007 | Spratt | |
| 2007/0299443 A1 | 12/2007 | DiPoto et al. | |
| 2008/0015582 A1 | 1/2008 | DiPoto et al. | |
| 2008/0039839 A1 | 2/2008 | Songer et al. | |
| 2008/0071274 A1 | 3/2008 | Ensign | |
| 2008/0071277 A1 | 3/2008 | Warnick | |
| 2008/0119849 A1 | 5/2008 | Beardsley et al. | |
| 2008/0172093 A1* | 7/2008 | Nilsson | 606/250 |
| 2008/0183215 A1 | 7/2008 | Altarac et al. | |
| 2008/0294194 A1* | 11/2008 | Capote et al. | 606/246 |
| 2008/0312703 A1 | 12/2008 | Hestad et al. | |
| 2009/0005814 A1 | 1/2009 | Miller et al. | |
| 2009/0036929 A1 | 2/2009 | Reglos et al. | |
| 2009/0082811 A1 | 3/2009 | Stad et al. | |
| 2009/0099604 A1 | 4/2009 | Cho et al. | |
| 2009/0099605 A1 | 4/2009 | Fallin et al. | |
| 2009/0177232 A1 | 7/2009 | Kiester | |
| 2009/0187217 A1 | 7/2009 | Weiman et al. | |
| 2009/0198279 A1 | 8/2009 | Zhang et al. | |
| 2009/0210007 A1 | 8/2009 | Levy et al. | |
| 2009/0216280 A1 | 8/2009 | Hutchinson | |
| 2009/0228046 A1 | 9/2009 | Garamszegi | |
| 2009/0299413 A1 | 12/2009 | Miller | |
| 2010/0004686 A1* | 1/2010 | Lemoine | 606/246 |
| 2010/0029884 A1 | 2/2010 | Simonson et al. | |
| 2010/0049252 A1 | 2/2010 | Smisson, III et al. | |
| 2010/0137915 A1 | 6/2010 | Anderson et al. | |
| 2010/0145389 A1 | 6/2010 | Triplett et al. | |
| 2010/0222822 A1 | 9/2010 | Farris et al. | |
| 2010/0249843 A1 | 9/2010 | Wegrzyn, III | |
| 2010/0256683 A1* | 10/2010 | Iott et al. | 606/278 |
| 2010/0268279 A1 | 10/2010 | Gabelberger et al. | |
| 2010/0292736 A1* | 11/2010 | Schwab | 606/278 |
| 2010/0298884 A1* | 11/2010 | Faizan et al. | 606/266 |
| 2010/0312279 A1 | 12/2010 | Gephart et al. | |
| 2010/0318131 A1 | 12/2010 | James et al. | |
| 2010/0324599 A1 | 12/2010 | Montello et al. | |
| 2011/0022088 A1 | 1/2011 | Forton et al. | |
| 2011/0087287 A1* | 4/2011 | Reeder et al. | 606/250 |
| 2011/0087288 A1 | 4/2011 | Stevenson et al. | |

(56) References Cited

U.S. PATENT DOCUMENTS

| | | |
|---|---|---|
| 2011/0106085 A1 | 5/2011 | Null et al. |
| 2011/0106164 A1 | 5/2011 | Wilcox et al. |
| 2011/0106166 A1 | 5/2011 | Keyer et al. |
| 2011/0166606 A1 | 7/2011 | Stihl et al. |
| 2011/0172717 A1 | 7/2011 | Miller |
| 2011/0190828 A1 | 8/2011 | Null et al. |
| 2011/0196426 A1 | 8/2011 | Peukert et al. |
| 2011/0270325 A1 | 11/2011 | Keyer et al. |
| 2011/0307018 A1 | 12/2011 | Zucherman et al. |
| 2011/0313323 A1 | 12/2011 | Henderson et al. |
| 2011/0313460 A1 | 12/2011 | McLean et al. |
| 2012/0010664 A1 | 1/2012 | Ritland |

* cited by examiner

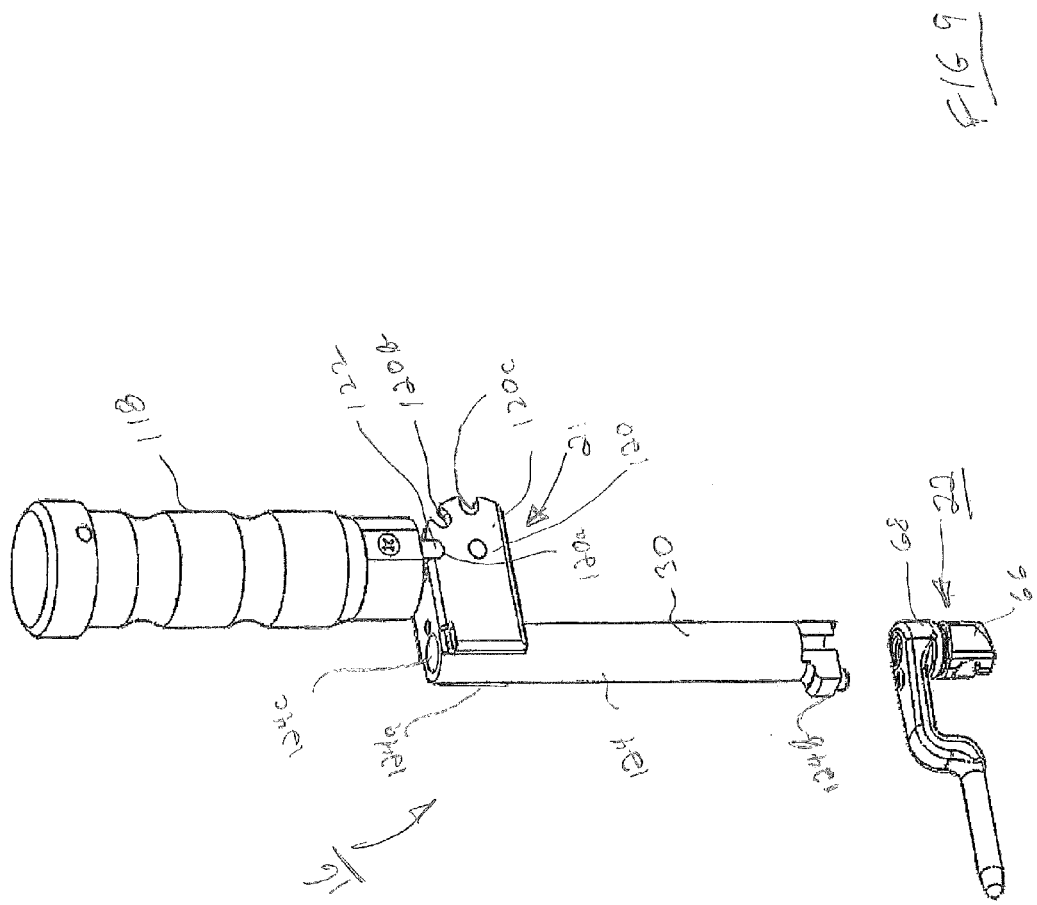

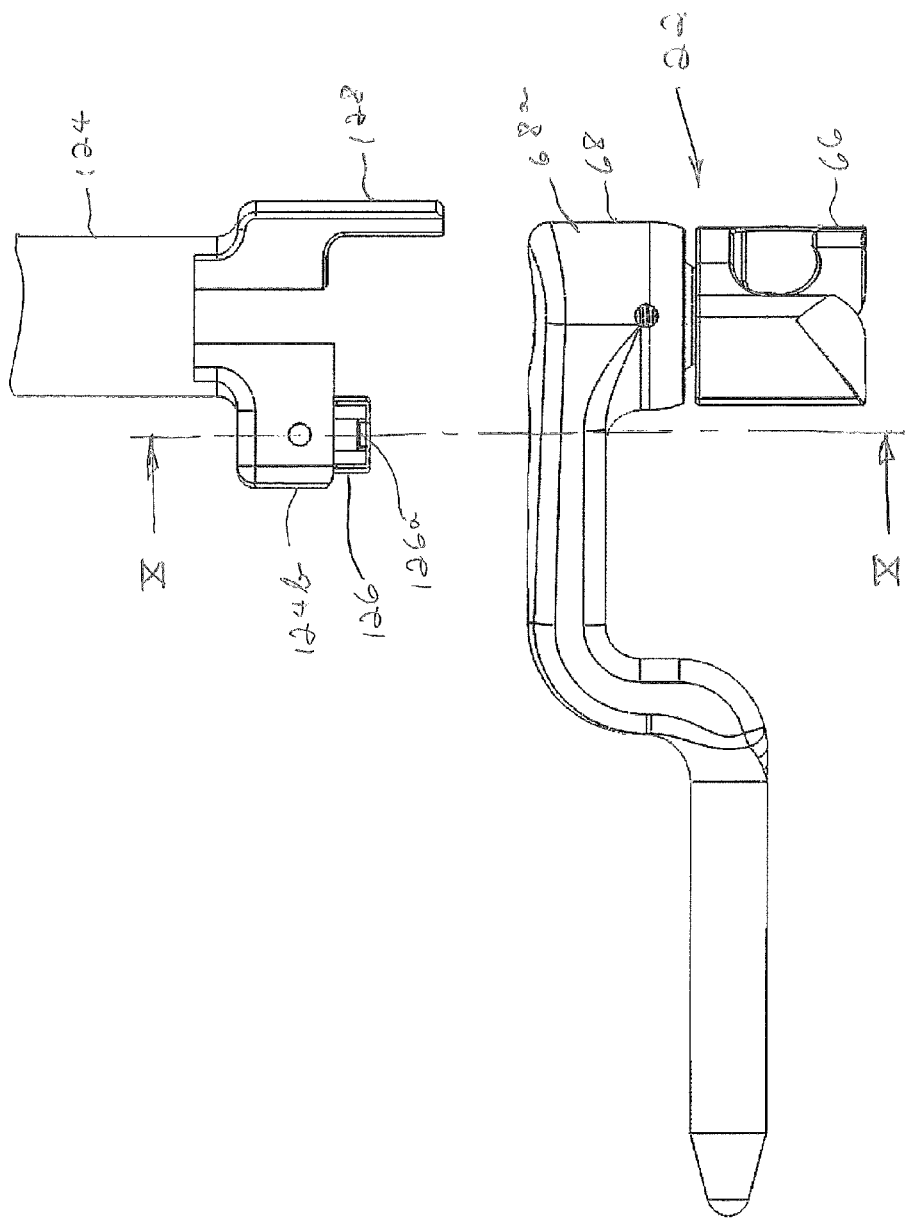

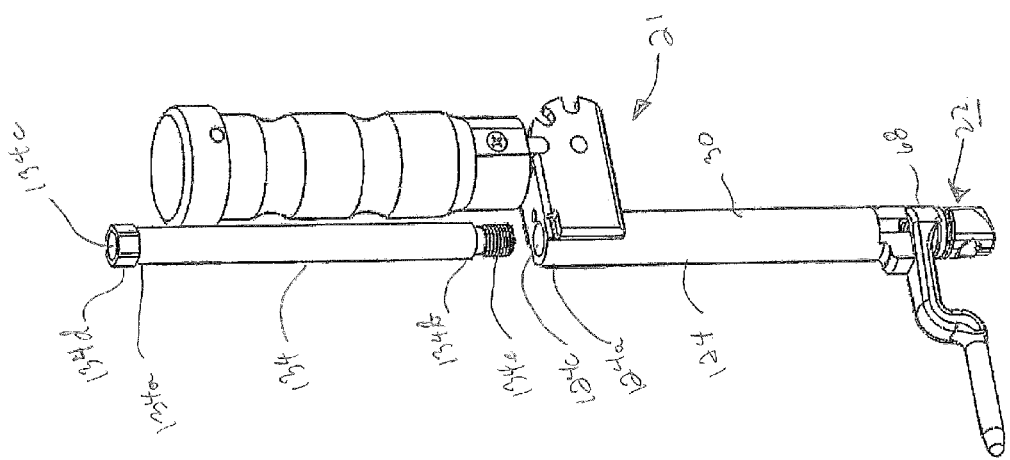

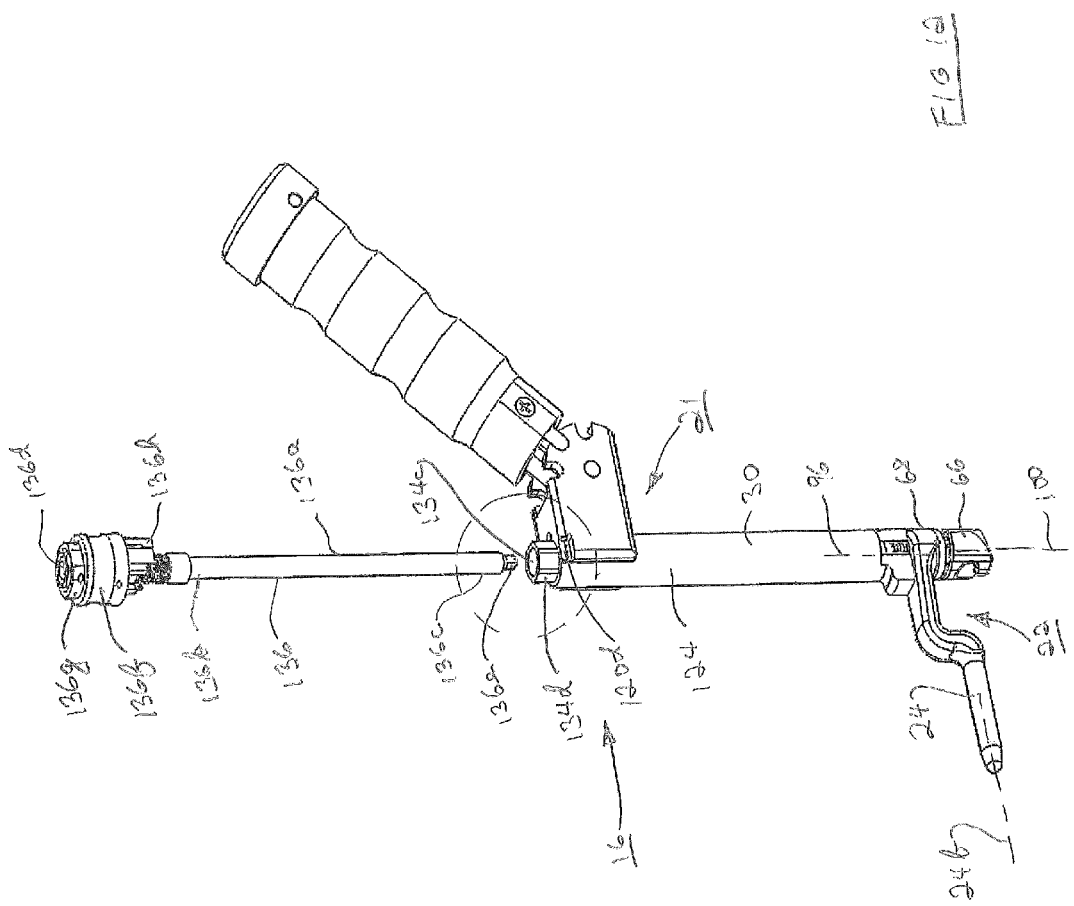

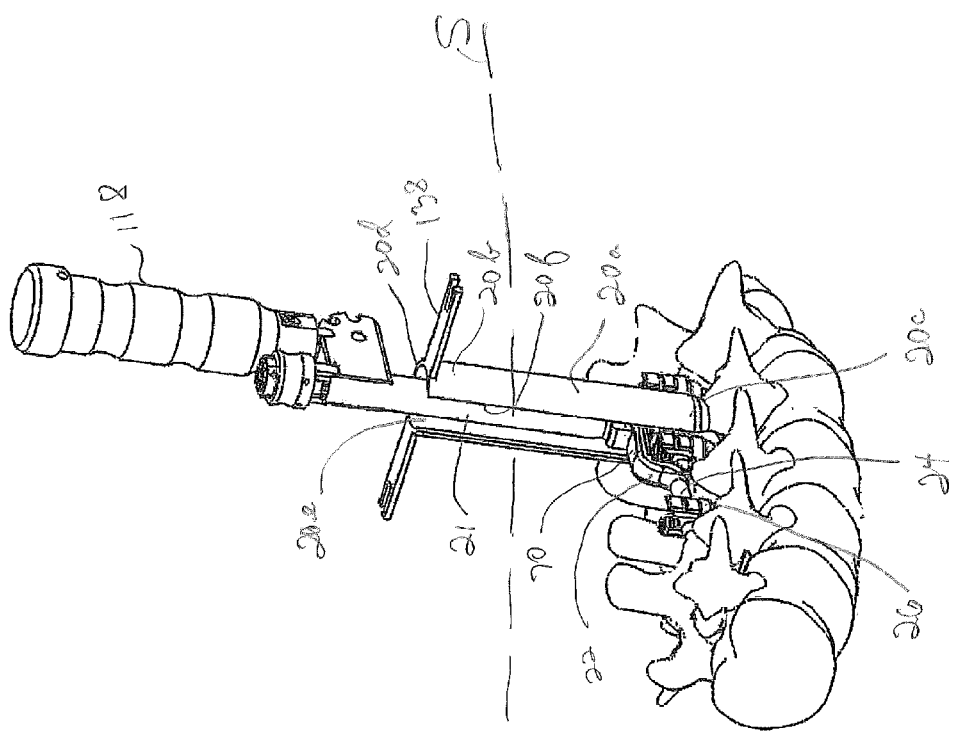

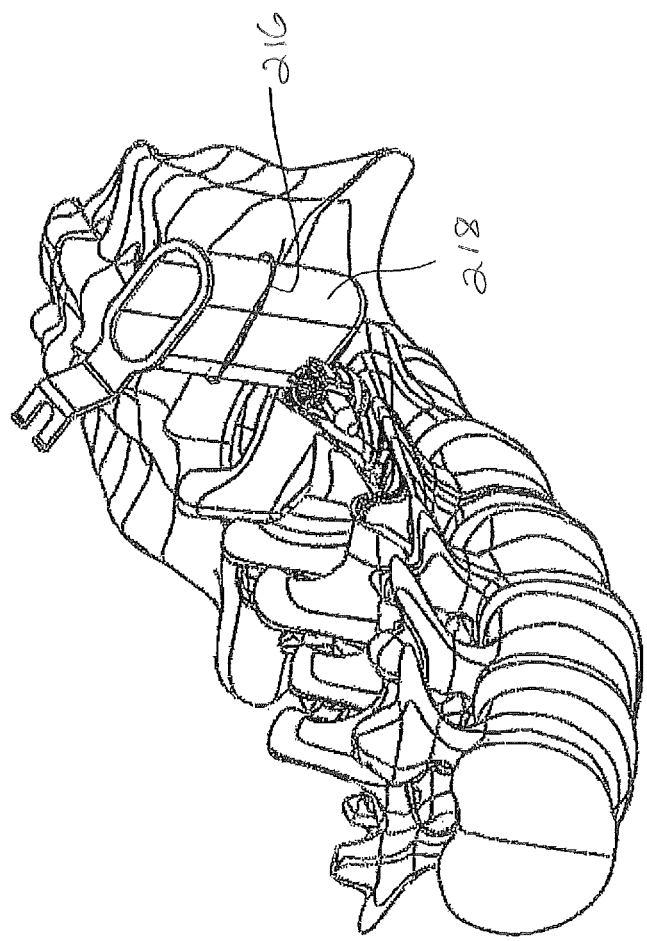

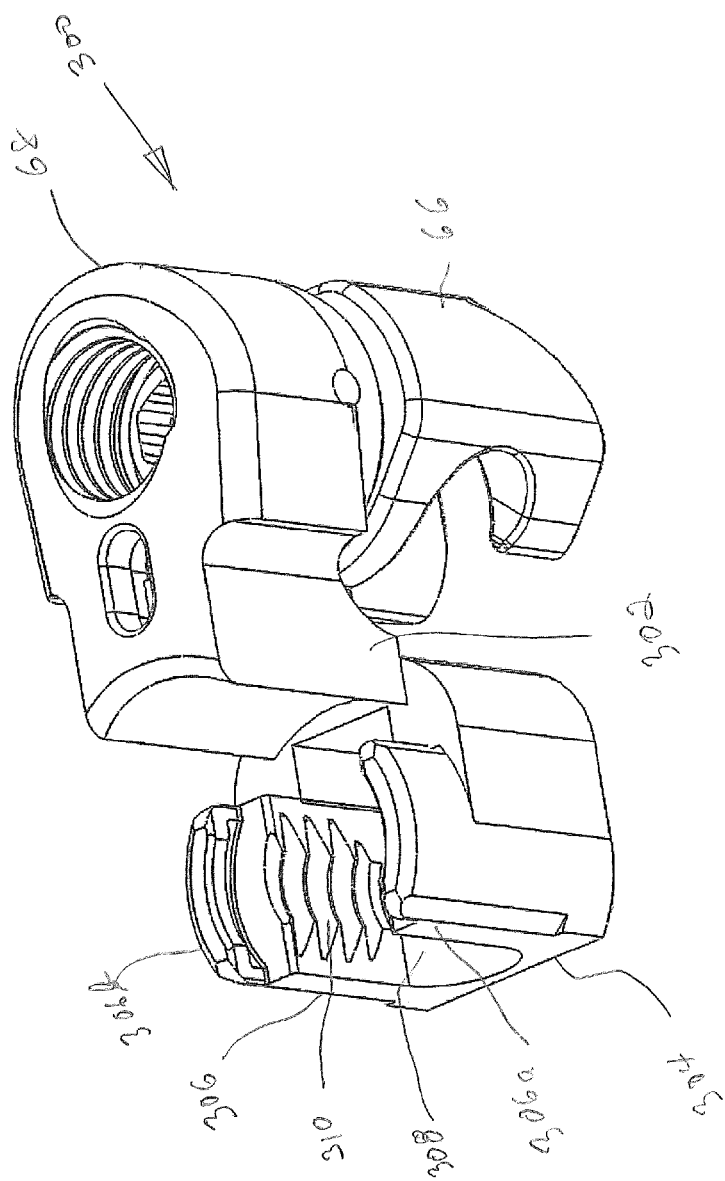

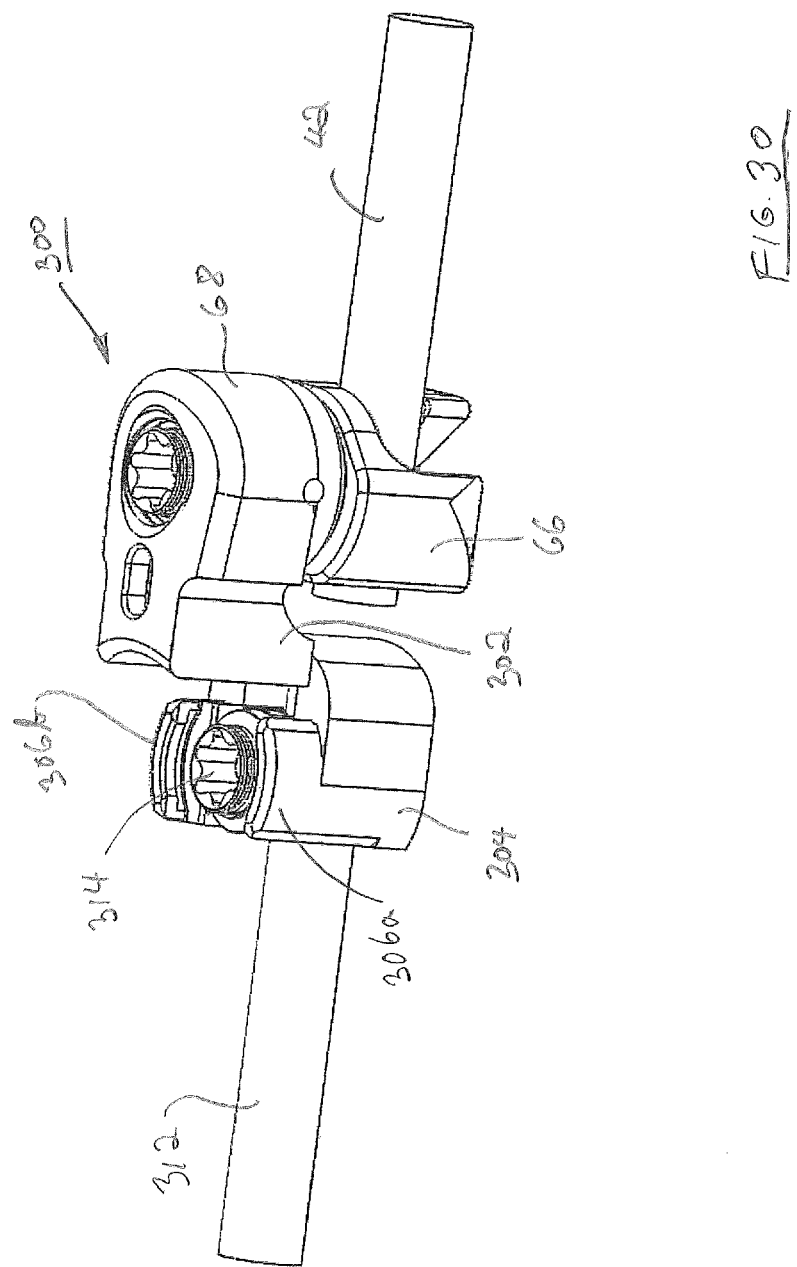

APPARATUS AND DEVICES FOR PERCUTANEOUSLY EXTENDING AN EXISTING SPINAL CONSTRUCT

CROSS-REFERENCES TO RELATED APPLICATIONS

This application is a divisional application of U.S. application Ser. No. 13/617,312, filed Sep. 14, 2012, now U.S. Pat. No. 8,523,906, which claims priority to U.S. Provisional Application No. 61/568,199, filed on Dec. 8, 2011, the entire contents of these applications being incorporated by reference herein.

BACKGROUND

The present disclosure contemplates devices and instrumentation for extending an existing spinal construct, and more particularly to procedures for achieving such extension minimally invasively, and preferably percutaneously.

An emerging trend in spinal fixation is an increased incidence of adjacent disc degeneration subsequent to a previous fixation or fusion. This subsequent degeneration often requires fixation or fusion of additional levels of the spine. It is common in current techniques to expose the entire prior construct to access all of the existing bone fasteners to permit removal of the connecting member spanning the fasteners. The connecting member is removed and replaced with a longer member, such as a rod, to engage an additional bone fastener added at the new levels to be instrumented.

This exposure of the prior fixation construct disrupts the existing construct complicating and lengthening the surgical procedure for adding the additional level of fixation. Such techniques are particularly problematic for a fixation construct spanning three or more vertebral levels. As such, there is a need for a device and method that facilitates the addition of further levels of fixation.

Several recent advancements have been disclosed that describe the extension of existing spinal constructs with minimal disruption to the existing construct. One example is shown in co-pending commonly assigned U.S. application Ser. No. 12/797,682, entitled "Devices and Methods for Adding an Additional Level of Fixation to an Existing Construct", filed on Jun. 10, 2010 and published as No. 2010/0318131. Other examples include U.S. Pat. No. 7,976,567, entitled "Orthopedic Revision Connector", issued on Jul. 12, 2011 to William B. Null, et al. and U.S. Pat. No. 8,021,399, entitled "Rod Extension for Extending Fusion Construct", issued on Sep. 20, 2011 to Stephen Ritland. While these approaches represent improvements in revision techniques and devices, it would be advantageous to not only extend an existing construct in a relatively non-disruptive manner to such construct, but to do so in a minimally invasively and, preferably percutaneous procedure.

SUMMARY

It is an object of the present invention to provide apparatus and devices for adding an additional construct to an existing spinal construct in a patient preferably minimally invasively and more preferably, percutaneously.

DESCRIPTION OF THE FIGURES

FIG. 9 is a top perspective exploded view of a rod connector extension assembly comprising a rod connector introducer and the rod connector of FIG. 4.

FIG. 10 is an enlarged side elevation view of the rod connector extension assembly of FIG. 9 showing details of the distal portion of the rod connector introducer positioned for releasable attachment to the rod connector.

FIG. 11 is a perspective view showing the assembled rod connector extension assembly of FIG. 9 with an inner sleeve positioned for insertion into the rod connector introducer.

FIG. 12 is a further perspective view of the assembled rod connector extension assembly of FIG. 11 with the inner sleeve received within the rod connector introducer and a hook rotator positioned for insertion into the inner sleeve.

FIG. 13 is a top perspective view of a portion of a patient's spine as viewed in the caudal direction showing the assembled rod connector extension assembly of FIG. 12 disposed within an access port.

FIG. 28 is a top perspective view of a portion of a patient's spine showing an oval access port positioned adjacent an existing spinal rod for receipt of the rod connector in the assembly shown in FIG. 27.

FIG. 29 a top perspective view of a second alternative arrangement of a rod connector for attachment to an existing spinal rod of an existing spinal construct of FIG. 1.

FIG. 30 is a further view of the second alternative rod connector of FIG. 29 showing an inline connection of an additional rod to an existing spinal rod.

DESCRIPTION OF THE EMBODIMENTS

Figure 1:
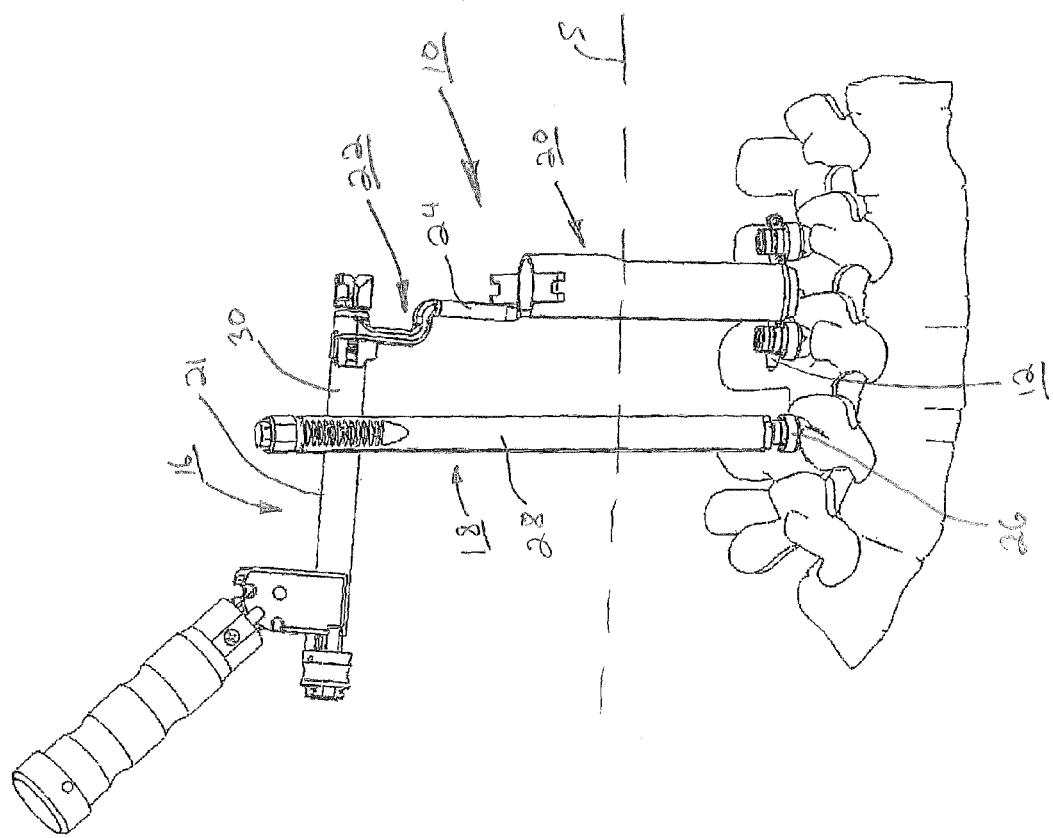
FIG. 1 is a side elevation view of a portion of a patient's spine showing instrumentation disclosed herein to extend an existing ipsilateral spinal construct.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
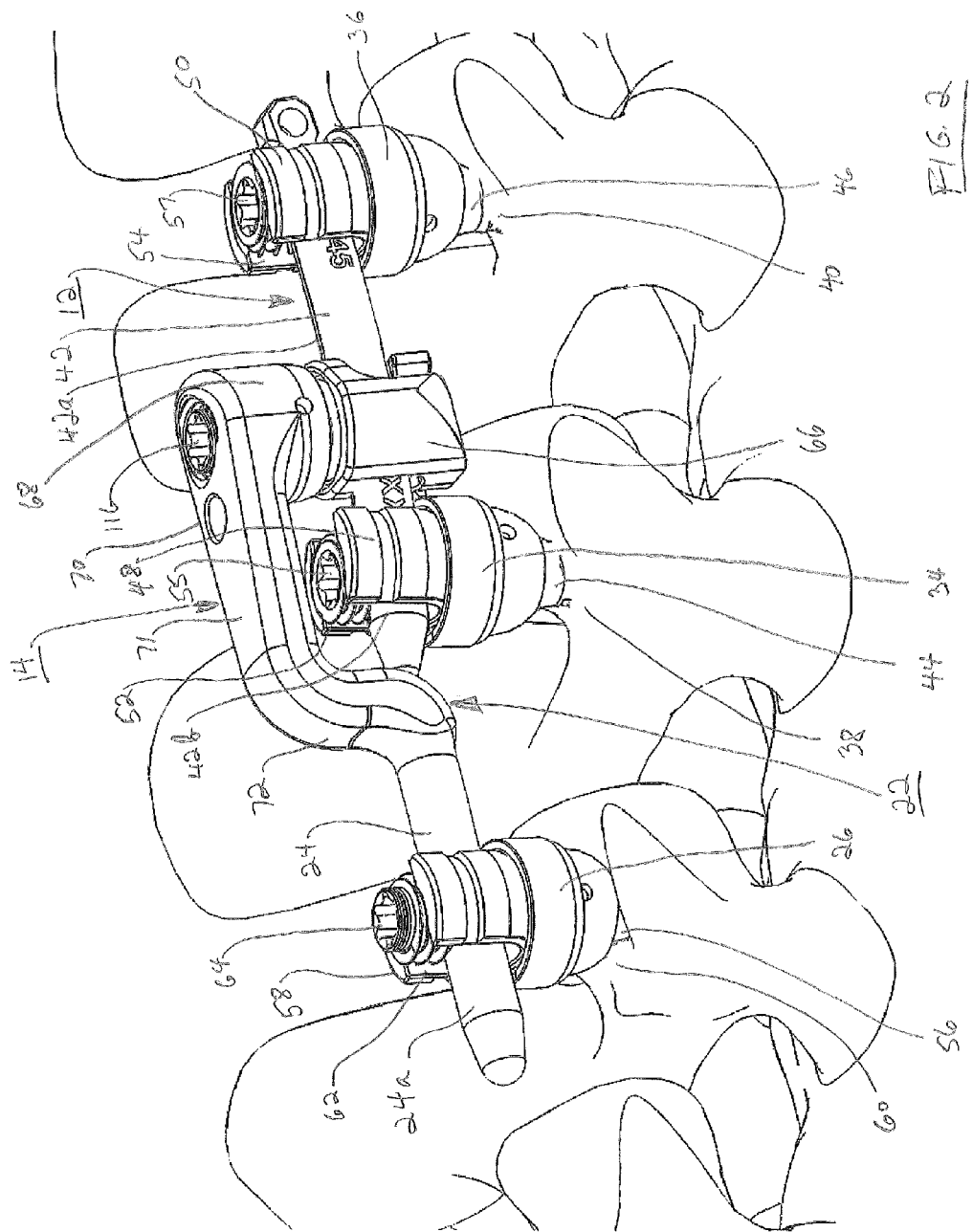
FIG. 2 is an enlarged perspective view of the existing spinal construct and inline extension of FIG. 1.

Referring to FIGS. 1 and 2, an apparatus 10 is shown for extending an existing spinal construct 12 by adding an additional spinal construct 14 so as to increase the level of spinal fixation in a patient having previously undergone spinal fusion or other spinal surgery. The apparatus 10 generally comprises a rod connector extension assembly 16, a spinal implant extension assembly 18 and an access port 20. Rod connector extension assembly 16 includes a rod connector introducer 21 and a rod connector 22 comprising an elongate additional spinal rod 24 serving as a connecting element, as will be described. Spinal implant extension assembly 18 comprises an additional spinal implant 26 and an elongate extension 28 releasably coupled thereto. As illustrated, the existing spinal construct 12 as well as the additional spinal construct 14 are located ipsilaterally in the spine in this particular arrangement. As will be described in more detail below, rod connector introducer 21 comprises an elongate extension 30 releasably attached to the rod connector 22. Each of extension 28 and access port 20 is sized and of length to be accessible outside the patient's skin. The patient's skin or fascia is depicted as a phantom line S for illustrative purposes only, with the understanding that the level of the fascia relative to the fixation location on the spine will vary from patient to patient. Spinal construct 12 is an existing spinal construct in the sense that it has been installed prior to the installation of the additional spinal construct 14 which means that existing spinal construct 12 may have been placed in a previous surgical procedure or may be placed during the same surgical procedure as, but prior to, additional spinal construct 14.

Turning to FIG. 2, further details of the additional spinal construct 14 and the existing spinal construct 12 are described. The existing spinal construct 12 comprises at least two previously implanted bone engaging implants 34 and 36 each of which is engaged respectively to a corresponding vertebra 38 and 40. Implants 34 and 36 are interconnected by an existing spinal rod 42 extending ipsilaterally therebetween. Existing spinal rod 42 includes an interconnecting portion 42a between implants 34 and 36 and an extending portion 42b projecting outwardly beyond implant 34, although extending portion 42b may also project in the opposite direction beyond implant 36. As shown, each of implants 34, 36 is a polyaxial pedicle screw having a lower threaded fastener portion 44, 46 for threaded engagement respectively in a pedicle of vertebra 38 and a pedicle of vertebra 40. Each implant 34, 36 includes a respective upper portion defining a yoke 48, 50 each yoke having a respective threaded slot 52, 54 for receipt of the existing spinal rod 42 therein. Set screws 55 and 57 respectively secure the existing spinal rod 42 to the implants 34 and 36.

The additional spinal construct 14 comprises rod connector 22 including elongate additional spinal rod 24, and a third bone engaging implant, namely additional spinal implant 26. Spinal implant 26, as depicted in FIG. 2, is a polyaxial pedicle screw having a lower threaded portion 56 and an upper yoke portion 58 that articulates relative to threaded portion 56. The threaded portion 56 is threadedly engaged to a third spinal segment 60 as will be described. As depicted, spinal segment 60 is another vertebral body, it being understood that such spinal segment may be segment S1 of the sacrum. The upper yoke portion 58 defines an open ended threaded slot 62 for receipt and support therein of the distal free end 24a of additional spinal rod 24 and is fastened to the yoke portion 58 by a set screw 64 or other suitable fastener. While additional spinal implant 26 is described as being a pedicle screw, it should be appreciated that depending upon the application additional spinal implant 26 may include other bone engaging implants with fasteners such as hooks, or rod connectors.

Figure 3:
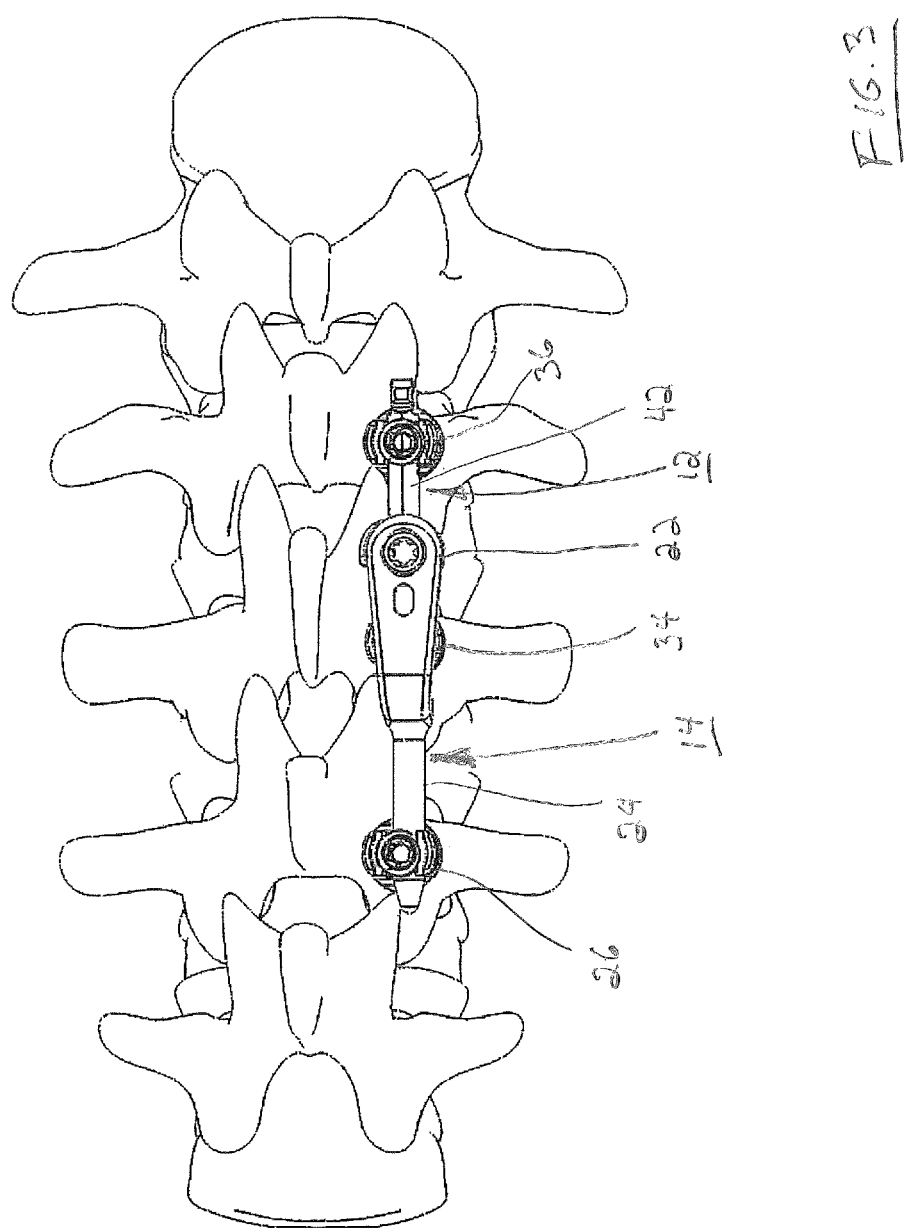
FIG. 3 is a top plan view of the existing spinal construct and inline extension of FIG. 1.
Figure 4:
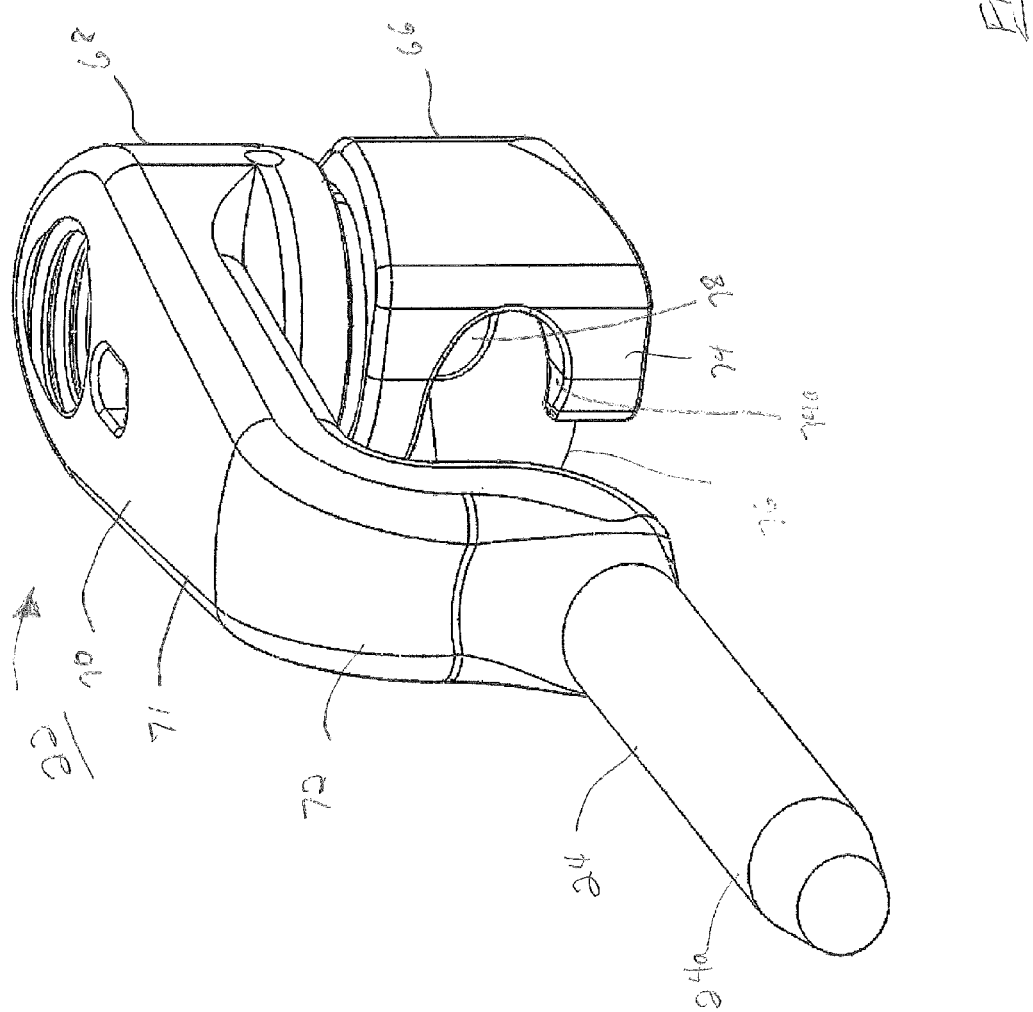
FIG. 4 is a top perspective view of a rod connector in accordance with one arrangement of the disclosure for attachment to an existing spinal rod of the existing spinal construct shown in FIG. 1.

Rod connector 22 comprises a lower first portion 66 and an upper second portion 68 articulatingly attached to the first portion 66. The first portion 66 is attached to the existing spinal rod 42 as will be further described. The second portion 68 includes a connecting portion 70 projecting therefrom that in the arrangement described defines the elongate additional rod 24 terminating in distal free end 24a. As illustrated in FIGS. 2 and 3 the additional spinal construct 14 is considered to be inline with the existing spinal construct 12. In such an arrangement, the upper second portion 68 of the rod connector 22 is positioned above and substantially in alignment with the axis of the existing spinal rod 42. The connecting portion 70 has a first extent 71 and a second offset extent defined by additional rod 24 with a jog 72 therebetween. Extent 71 is positioned above bone engaging implant 34 while the axis of additional spinal rod 24 is aligned generally parallel to and colinear with the axis of the existing spinal rod 42. As such, the existing spinal rod 42 and the additional spinal rod 24 are spaced approximately the same distance from a mid-line plane through the spine of a patient. It should be appreciated that depending upon the anatomy of the patient the orientation of the additional rod 24 relative to the existing rod 42 may differ.

Turning now to FIGS. 4-8, further the details of the rod connector 22 are described. The lower end of the first portion 66 of rod connector 22 comprises a pair of spaced hooks 74 and 76 each of which includes a respective projecting rod engagement member 74a and 76a. Hooks 74 and 76 are spaced from each other at a distance defining an opening 78 that allows the existing rod 42 to be received therebetween.

Figure 5:
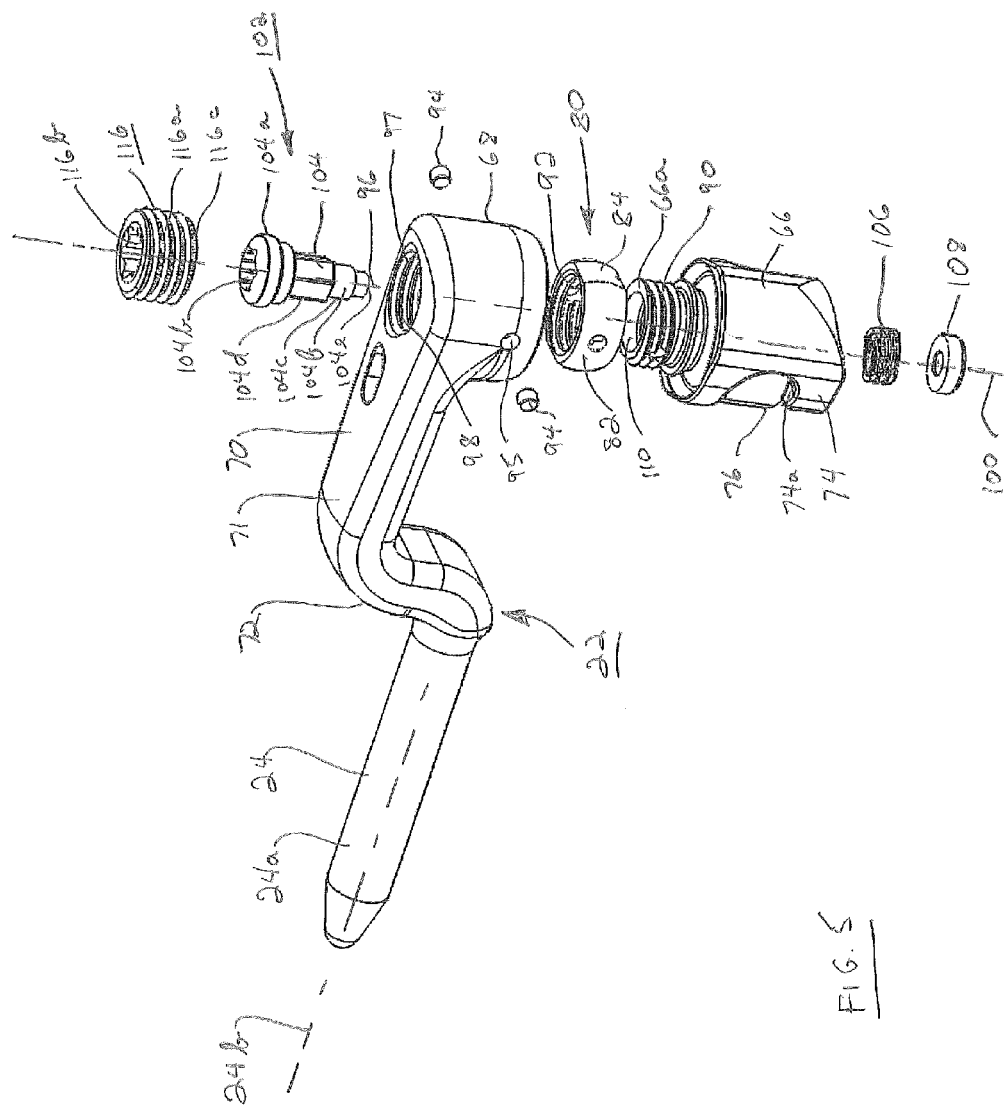
FIG. 5 is an exploded top perspective view of the rod connector of FIG. 4.
Figure 6:
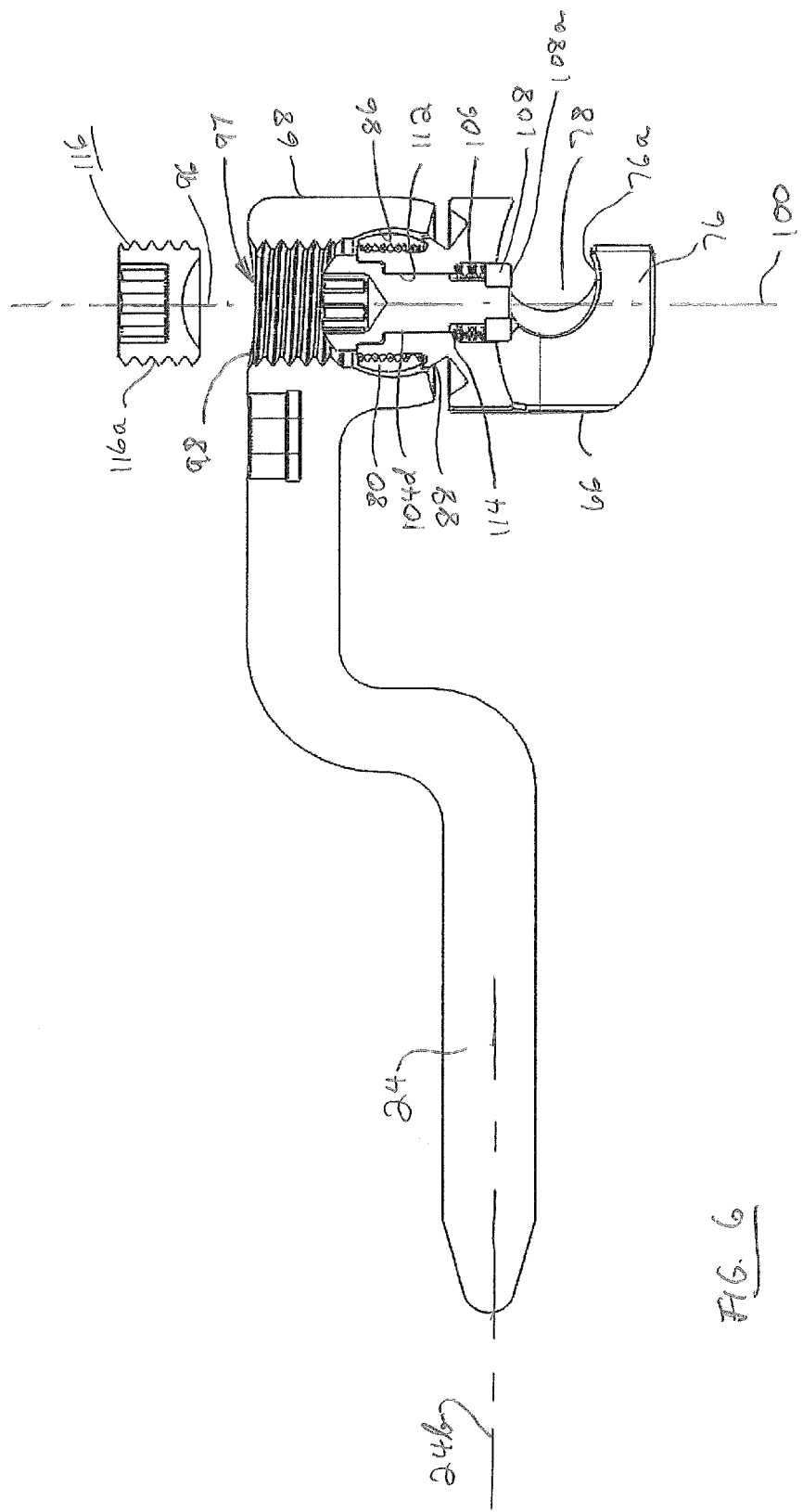
FIG. 6 is a longitudinal cross sectional view of the rod connector of FIG. 5.
Figure 7:
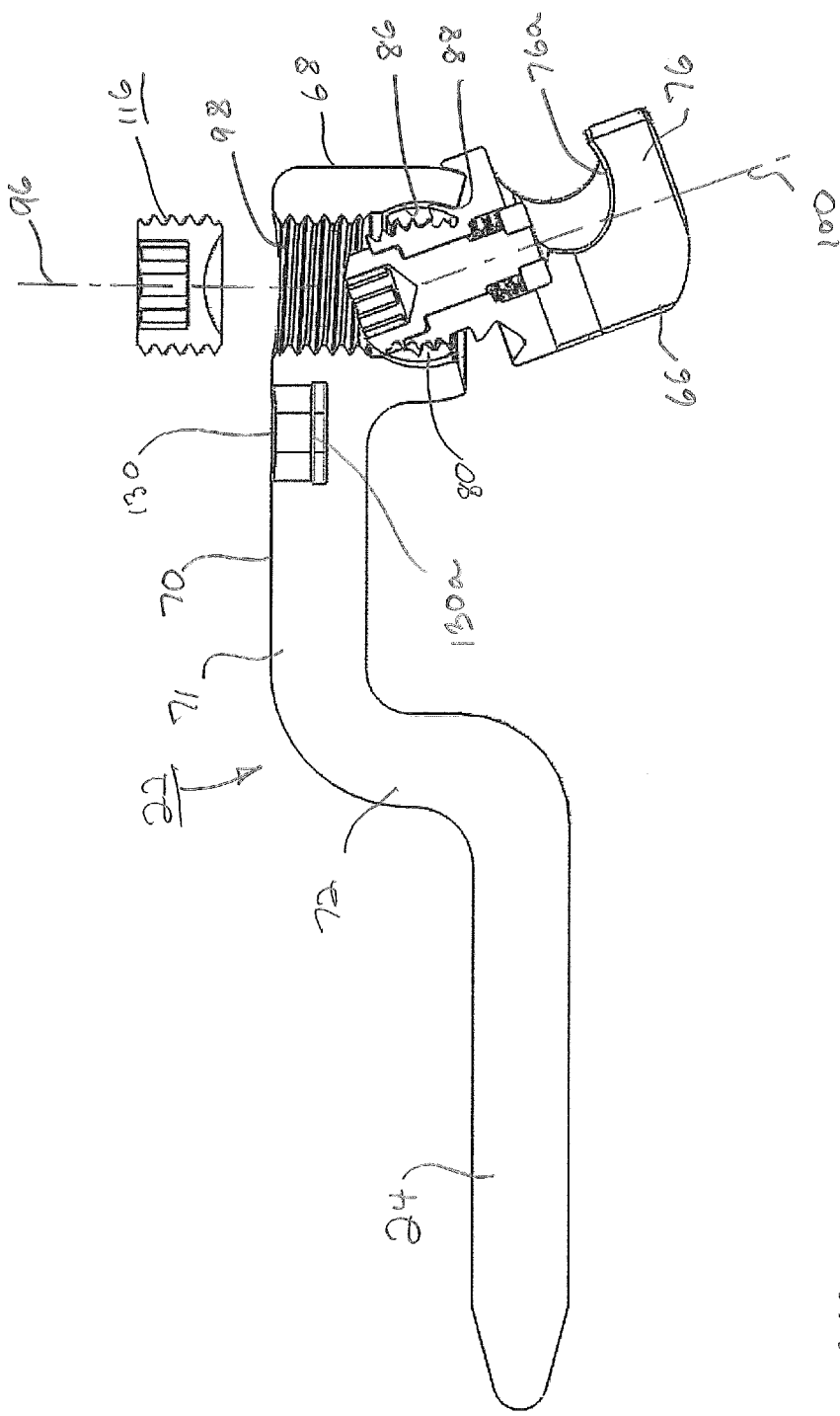
FIG. 7 is a view of the rod connector of FIG. 6 showing the hook portion having been articulated to a different angular position.

The first portion 66 of the rod connector 22 is attached to the second portion 68 by ball insert 80 which allows the first portion 66 to rotate and articulate relative to the second portion 68, as will be described. The ball insert 80 comprises a truncated sphere having a first outer spherical surface 82 and a second outer cylindrical surface 84, as shown in FIG. 5. The outer spherical surface 82 has a maximum diameter greater than the maximum diameter of the second outer cylindrical surface 84. The second portion 68 has an interior spherical surface 86 as shown in FIGS. 6 and 7 defining a socket for receipt of the spherical surface 82 of the ball insert 80. Interior spherical surface of socket 86 has a diameter slightly greater than the maximum diameter of first outer spherical surface 82 of the ball insert 80. The socket 86 has an entrance opening 88 that has a diameter less than the diameter of interior spherical surface of socket 86 and slightly greater than the maximum diameter of outer cylindrical surface 84 of the ball insert 80. The ball insert 80 is inserted through socket opening 88 along an axis of the ball insert 80 defined by a longitudinal axis of the outer cylindrical surface 84. As such, the ball insert 80 will pass through the socket opening 88 and into socket 86. Once therein, ball insert 80 is rotated 90° such that the outer spherical surface 82 is in sliding facing relationship with the interior spherical surface of socket 86. In this position, exterior threads 90 on an upper portion of the first portion 66 are threadably engaged into interior threads 92 of the ball insert 80. The ball insert 80 may be secured to the threads 90 of the first portion 66 to prevent loosening by locking pins 94 which may be installed through clearance openings 95 on opposite sides of first portion 68. The structure and operation of the ball insert 80 relative to socket 86 are fully described in commonly assigned U.S. application Ser. No. 11/560,587, entitled "Multi-axial Spinal Fixation System", filed on Nov. 16, 2006 and issued as U.S. Pat. No. 8,162,990, the disclosure of which is incorporated herein by reference in its entirety.

As described and as shown in FIGS. 6 and 7, the ball insert 80 and the joined rod connector first portion 66 can jointly articulate relative to the second portion 68 about axis 96 defined by the centerline of opening 97 having interior threads 98 extending into the second portion 68 in communication with spherical socket 86. In addition, first portion 66 can rotate relative to second portion 68 about an axis of engagement 100 defined by the centerline of exterior threads 90 of the first portion 66. In FIG. 6 the axis of engagement 100 and axis 96 of the second portion 68 are linearly aligned, while in FIG. 7, for example, the axis of engagement 100 is disposed at an angle with respect to axis 96 with first portion 66 having been articulated relative to second portion 68. In the position shown in FIG. 7, the first portion 66 is in an unlocked position and may still rotate about axis of engagement 100 so as to cause hooks 74 and 76 to engage existing rod 42, allowing greater flexibility for the attachment of the rod connector 22 to the existing rod 42.

Referring to FIGS. 5 and 6 a device for rotating the first portion 66 relative to the second portion 68 as well as for providing a provisional retention of the rod connector 22 to an existing rod 42 is described. A rotation element 102 supported by the first portion 66 comprises a rotation pin 104, a wave spring 106 and a retention ring 108. The rotation pin 104 comprises a head 104a having an internal hex socket 104b for receipt of the hook rotator, as will be described. Socket 104b may comprise other suitable socket configurations, such as a conventional Torx configuration. Rotation pin 104 further comprises a shank 104c having an upper outer hex surface 104d a distal outer cylindrical surface 104e and a larger intermediate cylindrical surface 104f between surfaces 104d and 104e. Surfaces 104d, 104e and 104f may also include other suitable configurations.

Figure 8:
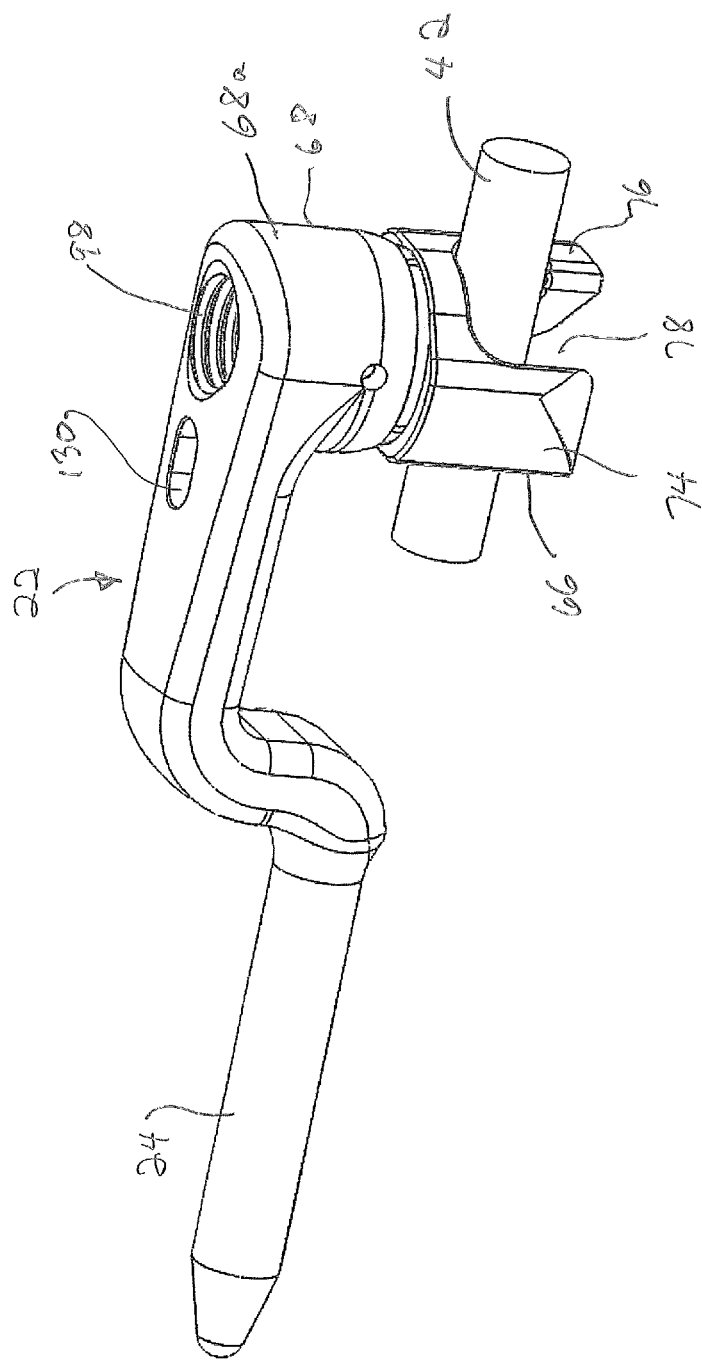
FIG. 8 is a further top perspective view of the rod connector of FIG. 4 showing the rod connector in an inline engagement with an existing spinal rod.

To assemble the rotation element 102 to the rod connector 22, the rotation pin 104 is inserted into opening 97 along axis 96 through threads 98 and into opening 110 interiorly of threads 90 of first portion 66. The interior surface 112 of opening 110 comprises a complementary hex configuration for matable receipt of the hex surface 104d of rotation pin 104. With such hex surfaces in engagement, rotation of the rotation pin 104 will cause rotation of the first portion 66. Wave spring 106 is placed over intermediate cylindrical surface 104f and retention ring 108 is placed over distal cylindrical surface 104e. Retention ring 108 is secured to distal cylindrical surface 104e by laser welding or other conventional joining techniques. Securement of the retention ring 108 to the rotation pin 104 compresses the wave spring 106 between the retention ring 108 and an inner surface 114 adjacent, and substantially orthogonal, to interior surface 112 of opening 110 in the first portion 66. As such, rotation element 102 is movably supported on said first portion 66 by wave spring 106 with the distal end of the retention ring 108 defining a rod engagement surface 108a normally biased into the opening 78 between the hooks 74 and 76 of the first portion 66. Such biased interference of the rod engagement surface 108a into opening 78 allows the existing rod 42 to be received into opening 78 and provisionally held by the rod engagement members 74a and 76a upon rotation of the hooks 74 and 76 under the bias of wave spring 106 as shown in FIG. 8. It should be appreciated that other spring elements, such as a helical spring, may be used as alternatives to wave spring 106.

While the rod connector 22 is provisionally retained to the existing rod 42 by the rod engagement members 74a and 76a under the bias of wave spring 106, this position is an unlocked position with rotation element 102 serving as a provisional holding element. A device for locking the rod connector 22 in a locked position relative to the existing rod 42 is described with further reference to FIGS. 5 and 6. A locking element such as a set screw 116 has exterior threads 116a for threadable rotational engagement with interior threads 98 extending within the second portion 68. The upper proximal end of the set screw 116 comprises a suitable socket, such as a Torx hexalobe socket 116b for receipt of a suitable tool for inserting and rotating set screw 116. The lower distal surface 116c is configured to engage the upper surface of head 104a of rotation pin 104 during rotational insertion. Continued insertion and tightening of the set screw 116 into threads 98 will cause the rod engagement surface 108a at the lower end of the rotation element 102 to forcibly engage the existing rod 42, effectively relieving the bias of wave spring 106 to thereby lock the first portion 66 to the existing rod 42. The force against the existing rod 42 also causes the first portion 66 and thereby the ball insert 80 to move downwardly relative to second portion 68 forcing the outer spherical surface 82 at the lower half of ball insert 80 tightly against interior spherical surface of socket 86 of second portion 68, thereby locking first portion 66 and second portion 68 securely together.

Referring still to FIGS. 4 through 7 further details of the rod connector 22 are described. Projecting outwardly from second portion 68 is a connecting element 70. In this arrangement, connecting element 70 includes first extent 71 and elongated additional rod 24 terminating in distal end 24*a*. Connecting element 70 includes a jog 72 between first extent 71 and additional rod 24 causing the additional rod 24 to be offset relative to the first extent 71 so as to accommodate spinal anatomy. It should be appreciated that the height of jog 72 may be varied to provide different offset dimensions between additional rod 24 and first extent 71. In some arrangements, jog 72 may be eliminated such that first extent 71 is colinear with additional rod 24. In addition, first extent 71 and/or additional rod 24 may be curved so as to accommodate different spinal anatomical conditions. In the arrangement shown, additional spinal rod 24 defines a longitudinal axis 24*b* that extends transverse to axis 96 of the second portion 68 of rod connector 22. In one application, for example, axis 24*b* may be disposed at an angle of approximately 90° with respect to axis 96, shown in FIGS. 5 and 6. In the arrangement shown, rod connector 22 is formed as a one-piece structure. Connecting element 70 including elongated additional rod 24 may be otherwise integrally attached to second portion 68 by any suitable fastening means, including without limitation, welding, brazing and screws.

Turning now to FIGS. 9-12, details of the free hand rod connector introducer 21 are described. Rod connector introducer 21 comprises an elongate hollow extension 30 and a handle 118 interconnected to extension by an offset bracket 120. Handle 118 may be selectively moved to different angular orientations by releasing and interlocking projection 122 into multiple grooves 120*a*, 120*b* and 120*c* in bracket 120. Three positions are shown, namely 0°, 45° and 90° with handle 118 being in the 0° position shown in FIG. 9 and in the 45° position as shown in FIG. 12. Other angular orientations may also be provided. Hollow extension 30 comprises an elongate outer sleeve 124 having a proximal end 124*a* and a distal end 124*b* with a lumen 124*c* extending fully longitudinally therethrough. Proximal end 124*a* is suitably attached to bracket 120 and distal end 124*b* is configured to secure releasably to the second portion 68 of the rod connector 22.

Figure 10A:
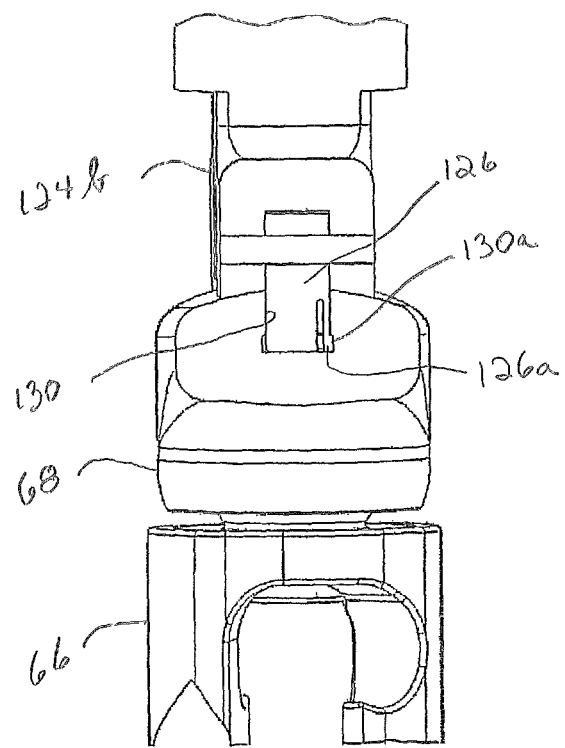
FIG. 10a is a cross sectional view of FIG. 10 as seen along viewing lines X-X of FIG. 10.

As illustrated in further detail in FIG. 10, the rod connector securement structure at the distal end 124*b* of sleeve 124 comprises a projecting attachment pin 126 and a skirt member 128 disposed diametrically opposite pin 126. Attachment pin 126 is of generally oval shaped configuration and comprises a flexible latch 126*a* projecting from a side surface of pin 126. Skirt member 128 projects axially downwardly from distal end 124*b* and has a concave inner surface configured to correspond to the outer curved surface 68*a* at one end of second portion 68. Attachment pin 126 is configured to be received in a complementary oval shaped hole 130 formed in an upper surface of second portion 68 of rod connector 22 (see FIGS. 7-8) with flexible latch 126*a* being releasably attached to a ledge 130*a* formed in a side wall of hole 130 in a snap-fit manner as shown in FIG. 10*a*. With attachment pin 126 received in hole 130 and skirt member 128 extending in close proximity around a portion of curved surface 68*a*, the outer sleeve 124 is substantially prevented from rotating relative to both the second portion 68 of rod connector 22 and elongate additional rod 24 which is integral with second portion 68. While attachment pin 126 and skirt member 128 are effective in releasably securing the outer sleeve 124 to the rod connector second portion 68, it should be appreciated that other releasable securement structure, such as screw threads, may be used.

Referring now to FIG. 11, rod connector introducer 21 is shown preliminarily attached to rod connector 22. To provide a more secure attachment, an inner elongate hollow sleeve 134 is included. Inner sleeve 134 has a proximal end 134*a* and a distal end with a lumen 134*c* extending fully longitudinally therethrough. Proximal end 134*a* terminates in a flange 134*d* having a hex surface for engagement with a wrench or other suitable tool. Distal end 134*b* comprises external threads 134*e* for threadable attachment with the interior threads 98 in the second portion 68 of rod connector 22. After outer sleeve 124 is preliminarily attached to rod connector 22, inner sleeve 134 is inserted through lumen 124*c* of sleeve 124 with threads 134*e* of the inner sleeve threadably engaging threads 98 in the second portion 68 of rod connector 22. Continued tightening of inner sleeve 134 causes flange 134*d* to engage an upper surface of distal end 124*a* of outer sleeve 124 thereby compressing the outer sleeve 124 between flange 134*d* and rod connector 22 for secure attachment thereto.

With extension 30 suitably releasably secured to rod connector 22, a hook rotator 136 is inserted into the lumen 134*c* in the inner sleeve 134, as shown in FIG. 12 to complete the rod connector extension assembly 16. Hook rotator 136 comprises an elongate shaft 136*a* having a proximal end 136*b* and a distal end 136*c*. Proximal end 136*b* includes a tool attachment surface 136*d* having a hex or other suitable configuration for engagement with a hand wrench 135 (see FIG. 21). Distal end 136*c* comprises an engagement surface 136*e* having a complementary mating configuration, such as hex configuration, for engagement with the socket 104*b* of rotation pin 104. As described above with reference to FIG. 5 rotation of the rotation pin 104 causes rotation of rod connector first portion 66 and hooks 74 and 76 projecting therefrom.

Hook rotator 136 includes at its proximal end a connection portion 136*f* and a ring 136*g*. Ring 136*g* is pinned to connection portion 136*f* to prevent relative rotation therebetween but is spring biased to allow axial translation when ring 136*g* is depressed distally. Ring 136*g* includes an internal hex surface that engages the hex surface of the tool attachment surface 136*d* when ring 136*g* is biased normally upwardly, thus preventing rotation. When ring 136*g* is depressed distally downwardly by a suitable tool such as by hand wrench 135, the internal hex surface of ring 136*g* disengages from the external hex surface of tool attachment surface 136*d*, thereby allowing rotation of the shaft 136*a* relative to connection portion 136*f*. Such disengagement allows the tool attachment surface 136*d* to engage a complementary hex surface (not shown) within the hand wrench 135 such that rotation of the hand wrench 135 rotates the elongate shaft 136*a*. Upon rotation of the shaft 136*a* by hand wrench 135 from outside the patient, the first portion 66 of the rod connector 22 and thereby hooks 74 and 76 are also rotated in a manner to effect connection of the rod connector 22 to existing rod 42, as will be described.

As hook rotator 136 is inserted into the lumen 134*c* of inner sleeve 134 engagement surface 136*e* is properly seated within the socket 104*b* of rotation pin 104. If proper seating is not achieved a marker or other suitable indicator may extend from the proximal end of elongate shaft 136*a* to inform the surgeon that engagement surface 136*e* is not properly inserted into socket 104*b*. The first portion 66 with hooks 74 and 76 may be rotated manually until proper seating is achieved. Upon such proper seating, connection portion 136*f* of hook rotator 136 is releasably attached to the bracket 120 at bracket portion 120*d* by a flexible portion 136*h*, as shown in FIG. 12 to hold connection portion 136*f* fixed relative to extension 30. As such, rotation of elongate shaft 136*a* relative to connection portion 136*f* also rotates shaft 136*a* relative to extension 30 and the rod connector 22 attached thereto. With the rod connector extension assembly 16 thus being assembled, longitudinal axis 24*b* of the elongate additional rod 24 projects outwardly from extension 30 and transverse to axis 96 of the second connector portion 68. In the arrangement shown, the angle between longitudinal axis 24*b* and axis 96 is substantially 90°. While a 90° angle is suitable, it should be appreciated that other angles may be contemplated.

Figure 12A:
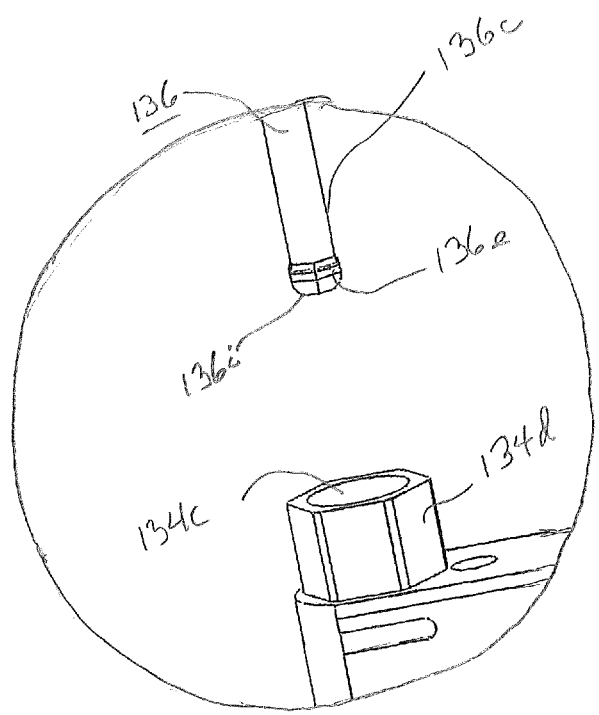
FIG. 12a is an enlarged view of the distal end of the hook rotator as encircled in FIG. 12.

In a preferred arrangement of rod connector extension assembly 16, hook rotator 136 is formed at its distal tip 136*i* as illustrated in FIG. 12*a* to have a curved configuration defining a ball hex shape. Thus, while the complementary mating configuration of engagement surface 136*e* is constructed to engage socket 104*b* and substantially prevents rotation unless shaft 136*a* is rotated, the ball hex shape will allow some articulation of the rod connector first portion 66 relative to second portion 68, as illustrated in FIG. 7, even when engagement surface 136*e* is seated within the socket 104*b* of rotation pin 104. With the rod connector first portion 66 being disposed at an angle with respect to rod connector second portion 68, first portion 66 may still be rotated about axis of engagement 100 by hook rotator 136. It should be understood that the distal tip 136*i* of rotator hook 136 may also be formed to be relatively flat such that when the complementary mating configuration of engagement surface 136*e* engages socket 104*b* there will be substantially no articulation of the first portion 66, with such first portion 66 being held generally fixed relative to the rod connector introducer 21 by the hook rotator 136.

Figure 14:
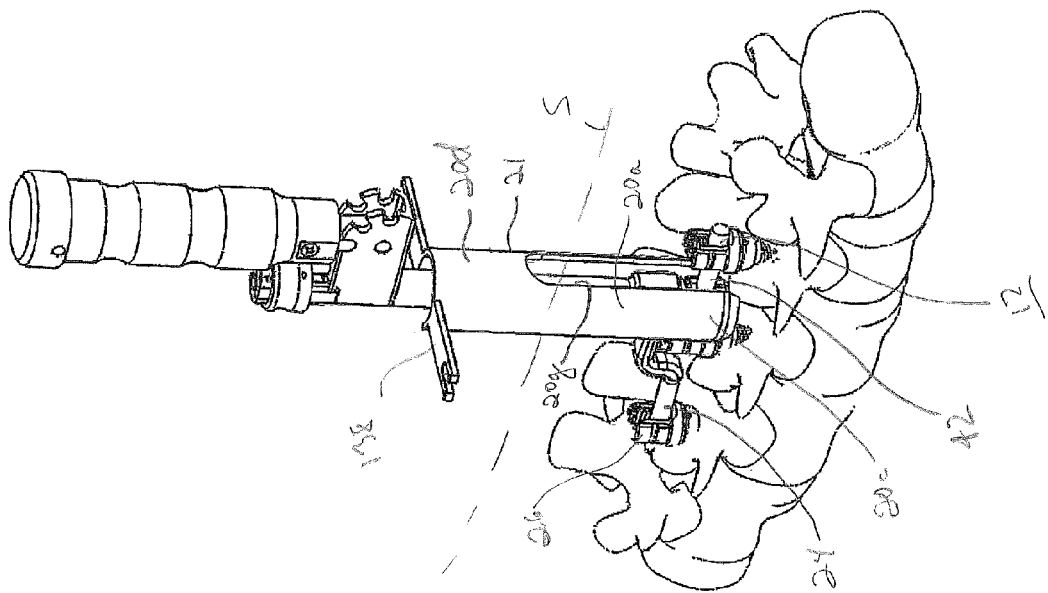
FIG. 14 is a top perspective view of FIG. 13 as viewed in the cephalad direction.

Turning now to FIGS. 13-14, details of the access port 20 are described. Access port 20 comprises an elongate sleeve 20*a* having a proximal end 20*b* and a distal end 20*c* for placement into the patient adjacent the existing spinal construct 12. The access port 20 is of length such that the proximal end 20*b* projects out from the patient's skin S when the distal end 20*c* is positioned adjacent existing construct 12. Sleeve 20*a* includes a perimetric sidewall 20*d* and a lumen 20*e* extending lengthwise therethrough. Lumen 20*e* is sized to receive the rod connector introducer 21 with the rod connector 22 secured thereto for attachment of the rod connector 22 to the existing spinal rod 42. Sleeve 20*a* has a slot 20*f* extending axially for a length through the sidewall 20*d* such that the slot 20*f* extends outside the patient when the distal end of the access port 20 is positioned adjacent existing construct 12. In the arrangement shown, slot 20*f* is arranged to face the additional spinal implant 26 to be implanted and extends axially fully through both the proximal end 20*b* and the distal end 20*c*. Slot 20*f* is sized and configured to receive therethrough the rod connector introducer 21 and the connecting portion 70 of rod connector 22 with the elongate additional rod 24 projecting therefrom. Slot 20*g* is formed diametrically opposite slot 20*f*, as shown in FIG. 14, slot 20*g* extending through distal end 20*c* and extending axially through perimetric sidewall 20*d* for a length that extends outside skin S of the patient. Slot 20*g* is sized and configured to receive therethrough at least a portion of the rod connector 22 and rod connector introducer 21 to accommodate rotation of the rod connector introducer 21, as will be described. A bracket 138 may be utilized to fix the access port 20 to an operating table in a conventional manner so as to maintain the access port 20 in place throughout the surgical procedure. While access port 20 is described in this arrangement as being generally tubular, it should be appreciated that access port may include other suitable structures such as by a pair of opposed blades defining a lumen therebetween, wherein the blades may be coupled at their proximal ends by a suitable ring or other coupling member.

Figure 15:
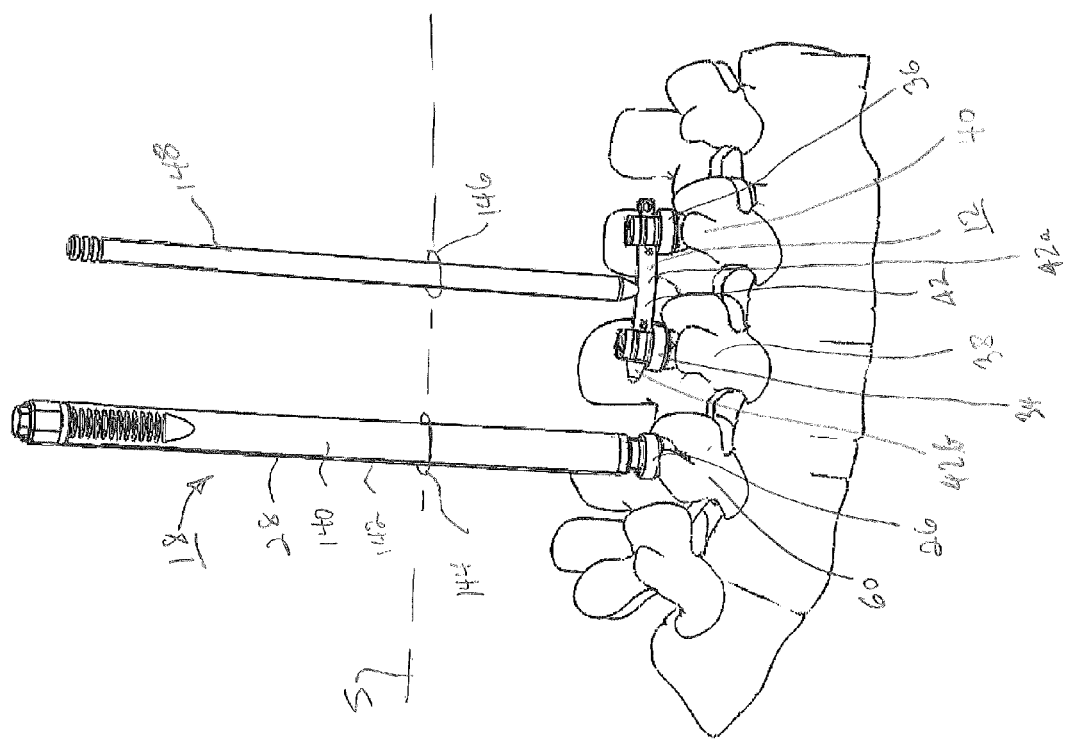
FIG. 15 is a side elevation view of a patient's spine showing instrumentation for targeting the position of an existing spinal construct within a patient and an additional spinal implant extension assembly spaced therefrom.

Having described the devices and instruments for extending an existing spinal rod construct in a patient, the procedures for such extension are now described with particular reference to FIGS. 15-23. The first procedure relates to percutaneously extending an existing spinal construct 12 as shown in FIG. 15 with an inline ipsilateral additional construct 14 as described above. The engagement of the additional spinal implant 26 as a component of the additional spinal rod construct 14 is described. Spinal implant extension assembly 18 comprises an elongate extension 28 which includes a hollow sleeve 140 releasably secured to the additional spinal implant 26. Spinal implant 26 is described as noted above with reference to FIG. 2 as being a polyaxial pedicle screw in this arrangement. Sleeve 140 has a pair of opposing slots 142 extending axially through the sleeve diametrically apart. The slots 142 are aligned and in communication with the slot 62 in the upper yoke portion 58 (see FIG. 2) of the spinal implant 26. The additional spinal implant 26 is percutaneously attached to the pedicle of the third spinal segment 60, which may be a segment of the sacrum 51 or another vertebral body. Additional spinal implant 26 is introduced through a small percutaneous incision 144 made through the skin S of the patient. The incision 144 is approximately 10-30 mm in length. The dilation of incision 144 and the percutaneous attachment of spinal implant 26 to a spinal segment such as vertebral body 60 is fully described in commonly assigned U.S. patent application Ser. No. 12/818,965, entitled "System for Percutaneously Fixing a Connecting Rod to a Spine", filed on Jun. 18, 2010, and issued as U.S. Pat. No. 8,142,437, (the '437 patent), the disclosure of which is incorporated herein by reference in its entirety. Once spinal implant 26 is attached to the vertebral body 60, the sleeve 140 as well as slots 142 project out from the patient through dilated incision 144 with the slots 142 being rotatably manipulable upon rotation of sleeve 140 to be aligned with slot 20*f* of access port 20 as will be described with reference to FIG. 16.

Figure 16:
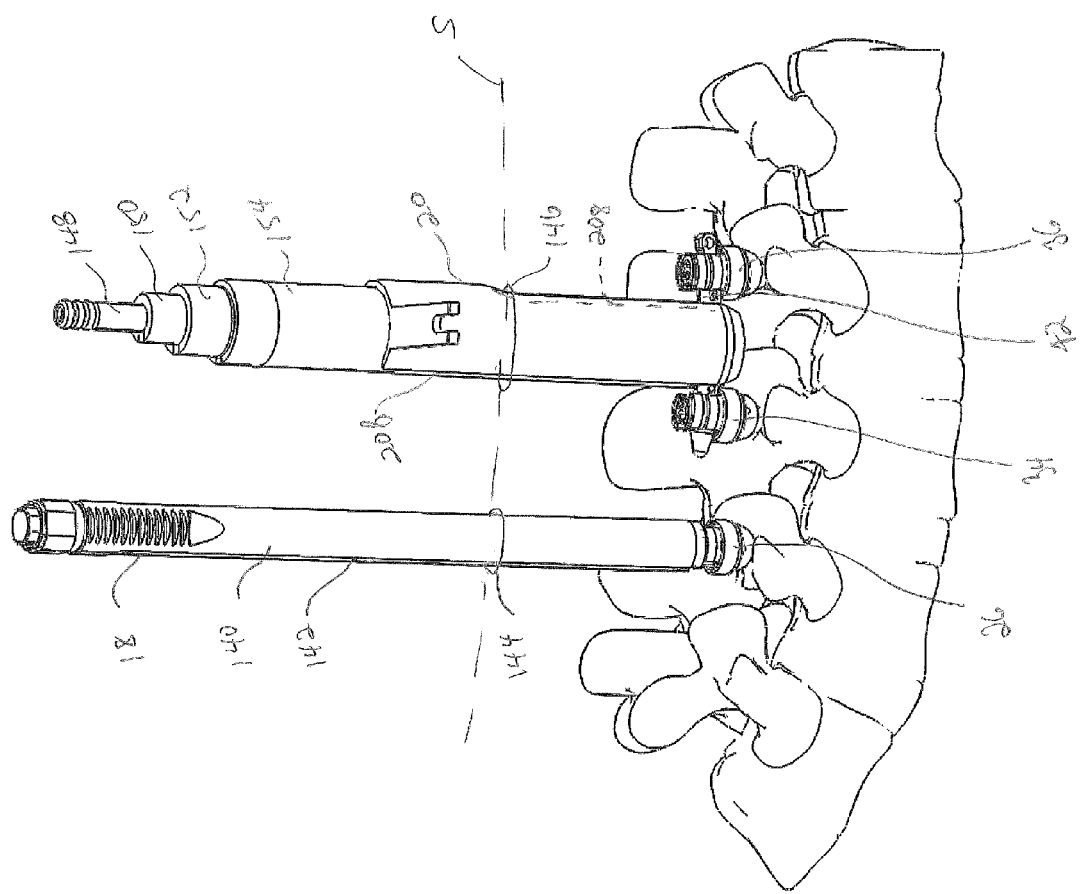
FIG. 16 is a further view of FIG. 15 showing dilating instruments including an access port for use in a percutaneous procedure for extending an existing spinal construct.
Figure 17:
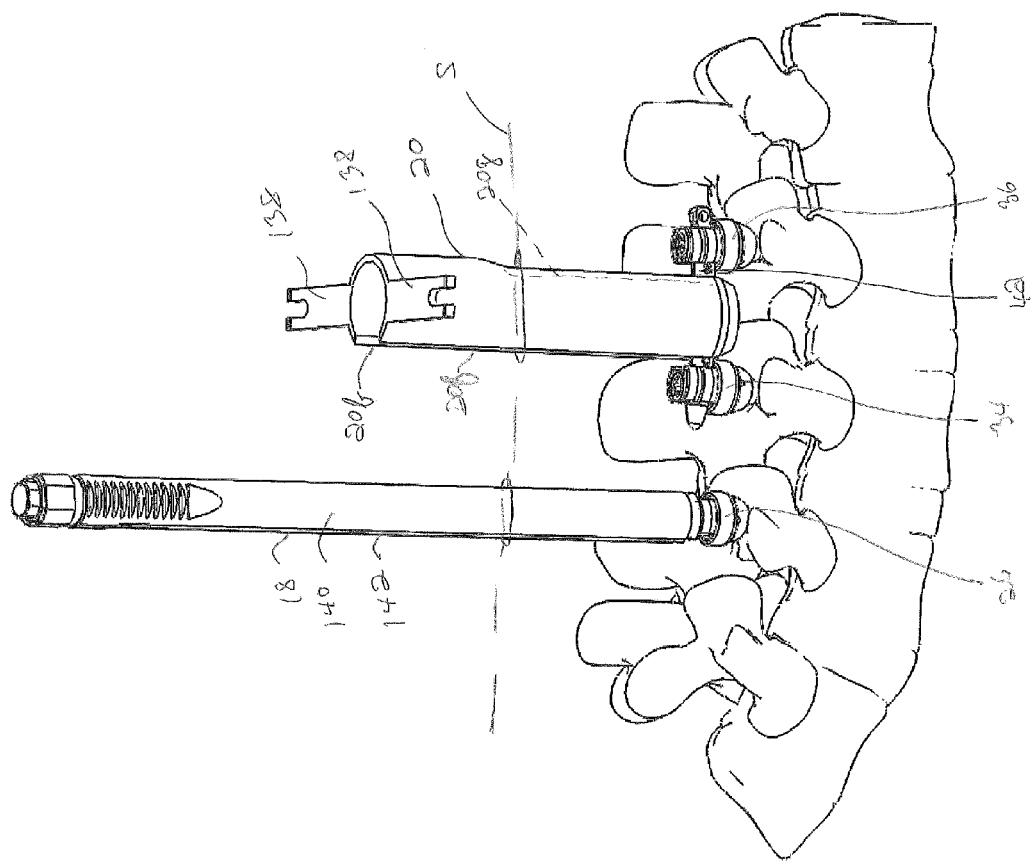
FIG. 17 is a further view of FIG. 16 with the dilating instruments removed and the access port positioned within the patient's spine adjacent the existing spinal construct.

Using fluoroscopy or other suitable imaging techniques, the existing spinal rod 42 is initially targeted so as to establish the position of the existing rod 42 in the patient. In this instance, the interconnecting portion 42*a* of existing rod 42 is targeted rather than extending portion 42*b* projecting outwardly beyond implant 34. A small percutaneous incision 146 is made through the skin S of the patient, the incision 146 being approximately 10-30 mm in length, although other suitable dimensions may be used. A targeting rod 148 is placed through the incised puncture and pushed through the tissue of the patient down to the existing spinal rod 42. Once the access path has been created and the position of the existing rod 42 established a series of sequentially increasing dilating instruments are inserted over the targeting rod 148. As depicted in FIG. 16, the dilating instruments include dilating cannulas 150, 152 and 154 of increasing diameter. The number of dilating cannulas may vary depending upon the procedure and the desired extent the incision 146 is to be expanded upon dilation. In addition, the dilating cannulas may include features that maintain the lateral position of such cannulas relative to existing rod 42 during insertion. Access port 20 is then finally placed over the last dilating cannula 154 with the opposing slots 20*f* and 20*g* communicating with existing rod 42 such that the distal end 20*c* of access port 20 straddles but does not attach to existing rod 42, as shown in FIG. 16. The dilating instruments are then removed as illustrated in FIG. 17 leaving the access port 20 in place. The central longitudinal axis of the access port 20 is generally aligned with and perpendicular to the longitudinal axis of existing rod 40. Bracket 138 may be utilized to fix the access port 20 to the operating table so as to maintain access port 20 fixed in place throughout the surgical procedure. The proximal end 20b of the access port 20 as well as slot 20f project out from the patient's skin, S, with access port slot 20f being generally aligned with and in facing relation to slots 142 of sleeve 140 in spinal implant extension assembly 18. Although also shown as extending outwardly of the patient's skin, S, slot 20g may be of length to lie below the patient's skin, S.

Figure 18:
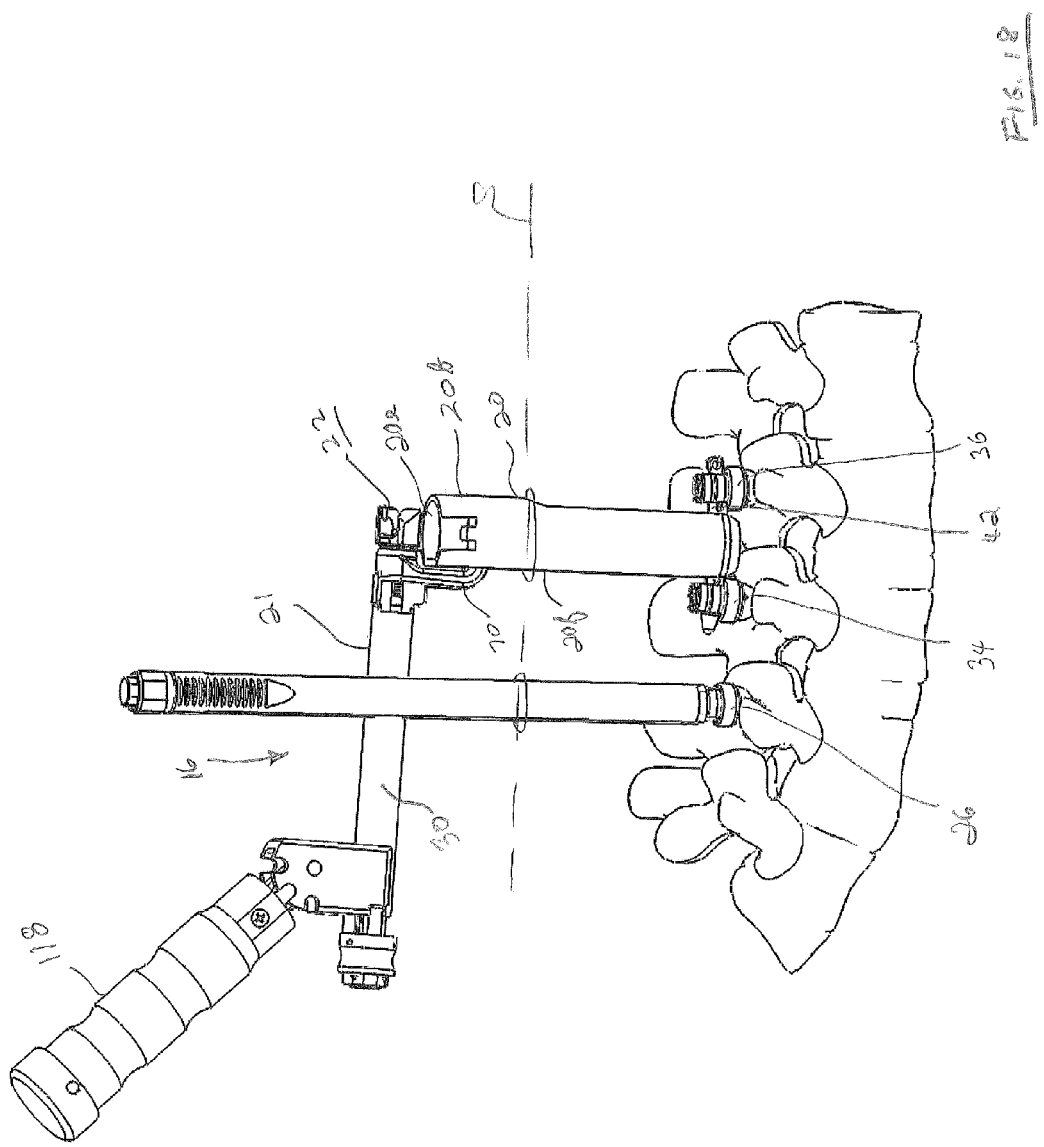
FIG. 18 is a side elevation view of the rod connector extension assembly positioned in the access port with the elongate additional rod of the rod connector being oriented in a first position generally parallel to the longitudinal axis of the access port.
Figure 19:
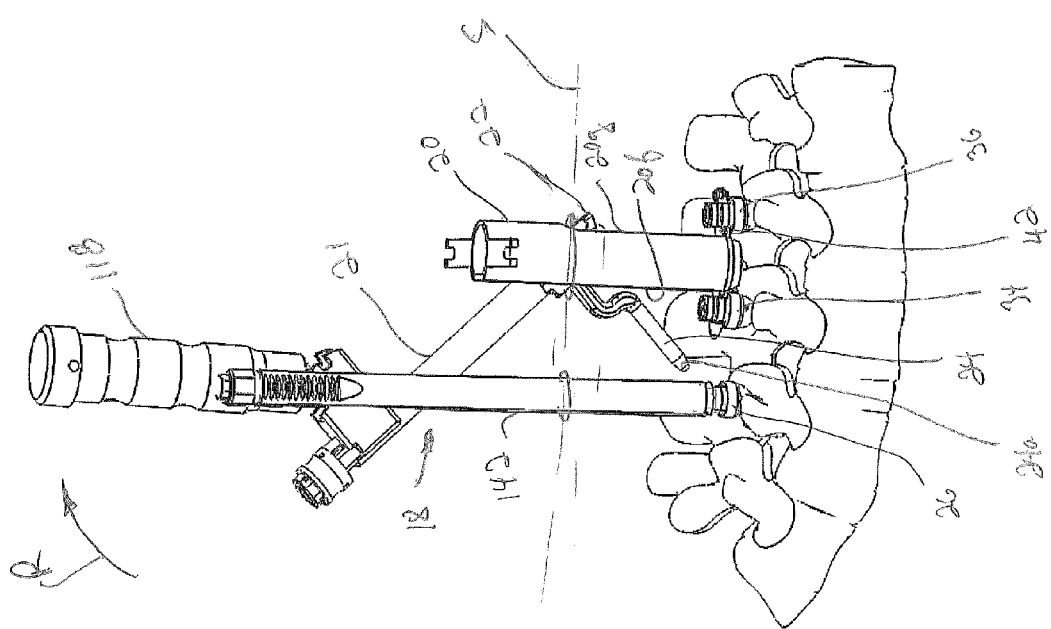
FIG. 19 is a further view of FIG. 18 showing the rotation of the rod connector introducer and the rod connector with the elongate additional rod being moved subcutaneously toward the additional spinal implant extension assembly.

By reference to FIG. 18 as well as to FIG. 1, the introduction of the rod connector 22 through manipulation of the rod connector extension assembly 16 is explained. The handle 118 may be in the 45° position for this stage of the procedure. With access port 20 fixed in place a surgeon grasps handle 118 and initially orients the extension 30 of rod connector introducer 21 generally parallel to the spine of the patient such that the axis 24b elongate additional rod 24 is oriented in a first position generally parallel to the longitudinal axis of access port 20. In this position, the additional rod 24 is within the lumen 20e of access port 20 with the connecting portion 70 of rod connector 22 extending through and projecting outwardly from slot 20f of access port 20. Through manipulation of rod connector introducer 21 the additional rod 24 is moved in this first orientation until the rod connector 22 is below the skin S of the patient. At this point, the rod connector introducer 21, with the access port slot 20f serving as a guide, is rotated so that additional rod 24 is rotated clockwise as viewed in FIG. 19 in a direction indicated by arrow, R.from its first orientation out from access slot 20f and toward sleeve 140 of spinal implant extension assembly 18. During such movement, the distal end 24a of additional rod 24 is subcutaneously moved through tissue of the patient beneath the skin S of the patient toward the sleeve 140 of spinal implant extension assembly 18.

Figure 20:
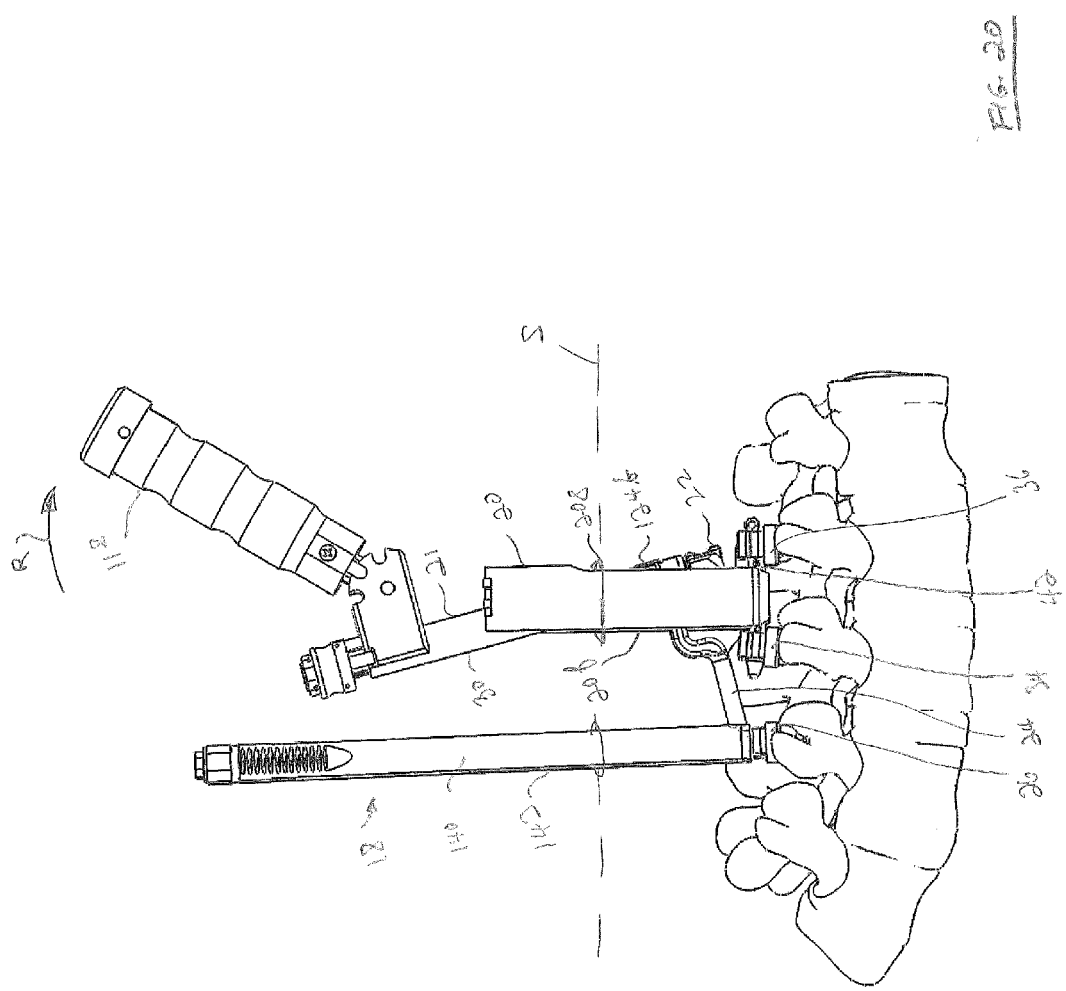
FIG. 20 is a further view of FIG. 19 showing further rotation of the rod connector introducer with the additional rod of the rod connector being introduced into a slot of the additional spinal implant extension assembly.

Continued rotation of handle 118 in the direction R further rotates rod connector introducer 21 until the distal end 24a of additional rod 24 approximates sleeve 140. With fluoroscopy the distal end 24a of additional rod 24 is guided into slot 142 that is in facing relationship with access port slot 20f, as shown in FIG. 20 for ultimate reduction into slot 62 of additional spinal implant 26. It should be appreciated that the additional rod distal end 24a may be directly received within slot 62 of additional spinal implant 26. During this portion of the rotation of rod connector introducer 21, the rod connector 22 as well as the distal end 124b of the rod connector introducer extension 30 may project outwardly from the opposite access port slot 20g to accommodate the rotation of rod connector introducer 21.

Figure 21:
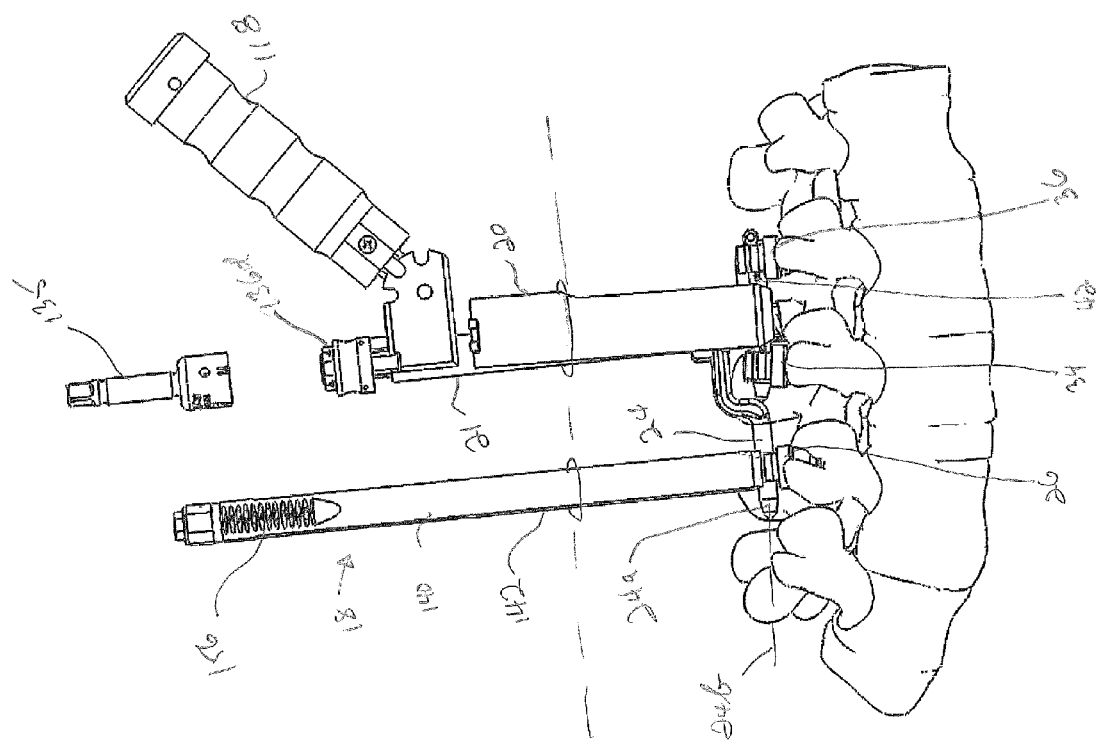
FIG. 21 is a further view of FIG. 20 showing final rotation of the rod connector introducer with the additional rod of the rod connector having been moved to a second different orientation transverse to the longitudinal axis of the access port and the distal portion of the additional rod extending through slots in the additional spinal implant extension assembly.

Upon final rotation of rod connector introducer 21 by handle 118 as shown in FIG. 21 the distal end 24a of additional rod 24 extends through both slots 142 of sleeve 140 and is either situated in slot 62 of additional spinal implant 26 (FIG. 2) or closely thereto. In this position the additional rod 24 has been moved to a second different orientation such that the axis 24b is transverse, and substantially perpendicular, to the longitudinal axis of access port 20. Also with the aid of fluoroscopy, the rod connector 22 at this point receives the existing spinal rod 42 within the opening 78 between hooks 74 and 76 of rod connector first portion 66. As described above, with first portion 66 capable of articulating while being held against rotation by the hook rotator 136, proper receipt of existing spinal rod 42 within opening 78 is achieved even if the longitudinal axis of rod connector introducer 21 is not precisely perpendicular to the axis of existing rod 42 thus allowing for potential irregularities of the spine. In this position, existing spinal rod 42 is in an unlocked position with respect to rod connector 22. Prior to rotation of rod connector hooks 74 and 76 to engage existing rod 42 for locking, the surgeon may, if necessary, reduce the additional rod 24 into slot 62 of additional spinal implant 26. Such reduction may be achieved by connecting a rod persuader (not shown) to a rod persuader coupling member 156 disposed at the proximal and of sleeve 140. The rod persuader including its structure and cooperation with rod persuader coupling member 156 is fully described in the '437 patent, the disclosure of which is incorporated herein by reference in its entirety.

With continued reference to FIG. 21 as well as to FIGS. 5-6, the engagement of the rod connector 22 to the existing spinal rod 42 is described. Hand wrench 135 is used to suitably depress ring 136g for attachment to tool attachment surface 136d as described above and is rotated either by hand or an appropriate tool. Rotation of wrench 135 rotates hook rotator shaft 136a as well as engagement surface 136e which is engaged within socket 104b of rotation pin 104. Upon such rotation of the shaft 136a, the rotation pin 104 rotates the first portion 66 of the rod connector 22 about the axis of engagement 100 in a manner to facilitate alignment of opening 78 relative to existing rod 42. Hooks 74 and 76 and the respective rod engagement member 74a and 76a are then rotated in a manner to engage the existing rod 42. As the hooks 74 and 76 are rotated, the engagement surface 108a at the distal end of rotation element 102 engages the existing rod 42 under the bias of wave spring 106 pushing the head 104a of the rotation pin 104 slightly upwardly into opening 97 of first portion 66. During such rotation the existing rod 42 is thereby received between the rod engagement member 74a and 76a and rotation pin engagement surface 108a in a snap-fitting movement that provides a tactile and potentially an audio indication to the surgeon that the existing rod 42 is properly seated in the rod connector 22 in a provisional engagement whereby the rod connector 22 is held on but not locked to the existing rod 42. Rod connector first portion 66 is rotated approximately 60° with respect to second portion 68 to establish such provisional engagement. It should be understood that first portion 66 may be rotated relative to second portion 68 at other angles which may be less than 60° or up to approximately 90°.

Figure 22:
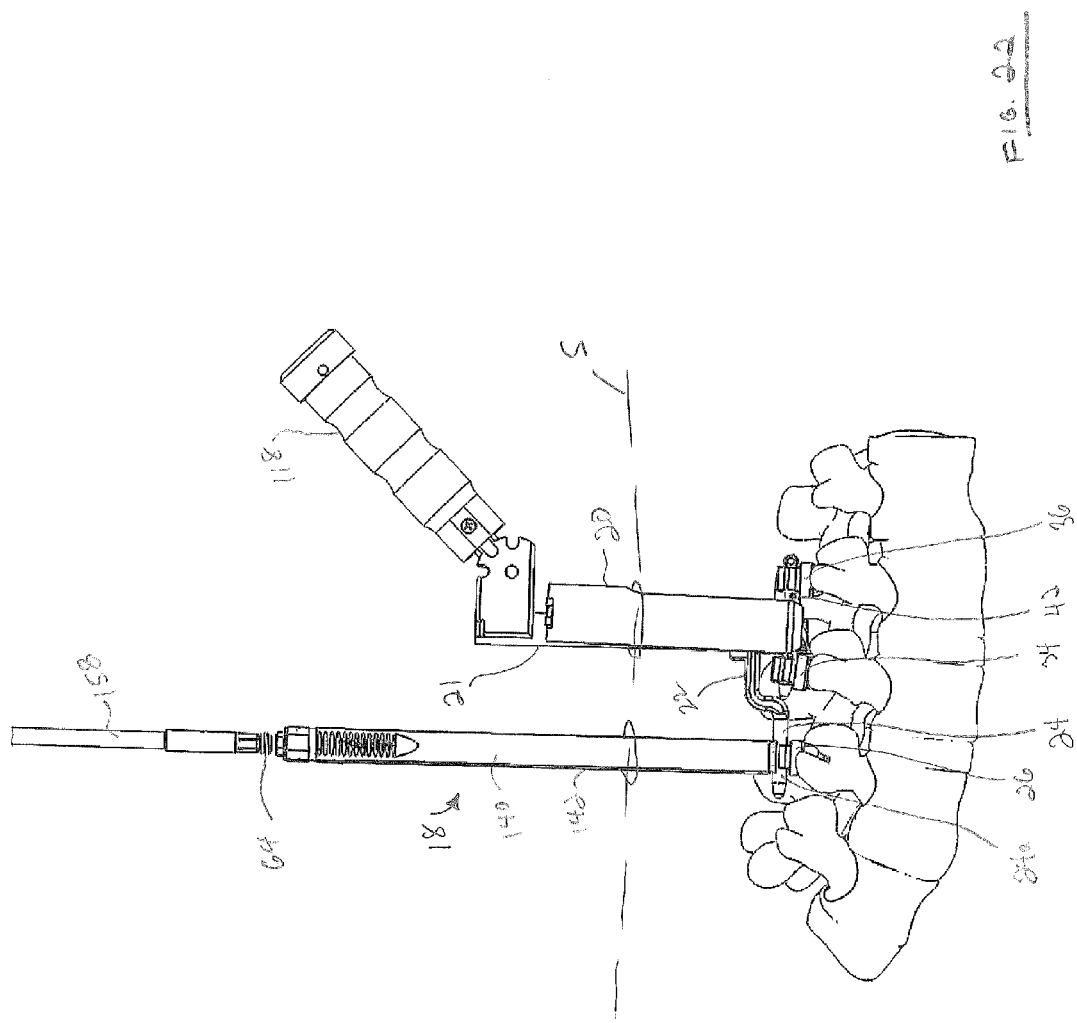
FIG. 22 is a view of FIG. 21 with the hook rotator and inner sleeve having been removed from the rod connector introducer and a driver instrument positioned to introduce a set screw through the additional spinal implant extension assembly for securing the additional rod of the rod connector to the additional spinal implant.

Once the rod connector 22 has been rotated to the provisional engagement position, the distal end 24a of additional rod 24 may then be secured to additional spinal implant 26 as described with reference to FIG. 22. Set screw 64 is suitably attached to a driver instrument 158 and sized and configured to introduce the set screw 64 with instrument 158 attached thereto into and through hollow sleeve 140 until set screw 64 engages the threads in the slot 62 of the upper yoke portion 58. Set screw 64 is tightened by rotation of instrument 158 to secure the additional rod 24 to the additional spinal implant 26. Instrument 158 is then detached from set screw 64 and removed from sleeve 140.

Figure 23:
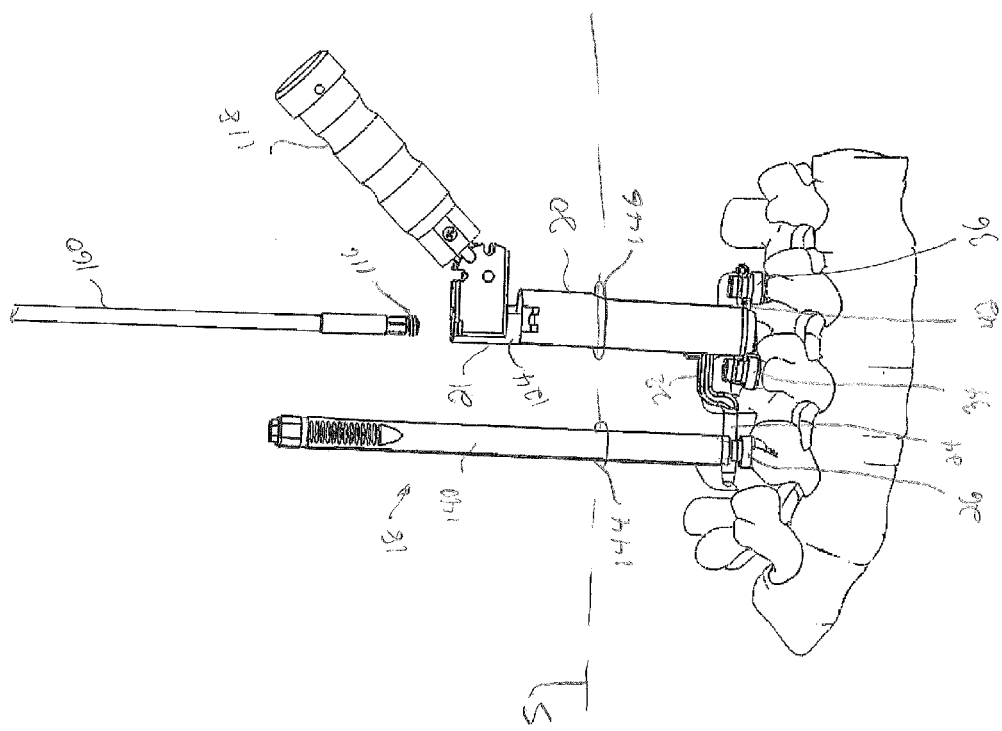
FIG. 23 is a view of FIG. 22 with the driver instrument removed and a driver tool positioned to introduce a set screw through the rod connector introducer for securing the rod connector to the existing spinal rod.

Turning now to FIG. 23 as well as to FIGS. 5-6 and 11, locking of the rod connector 22 to additional rod 42 is described. After removing hook rotator 136 and inner sleeve 134 from rod connector introducer 21, set screw 116 is suitably attached to a driver tool 160 with the distal tip of tool 160 in engagement with socket 116b of set screw 116. Tool 160 with set screw 116 attached thereto is sized and configured to be received within lumen 124c of outer sleeve 124 of rod connector introducer 21 until set screw 116 engages the threads 98 in rod connector second portion 68. As noted above, the lower distal surface 116c of set screw 116 engages the upper surface of head 104a of rotation pin 104 during rotational insertion of set screw 116. Continued insertion and tightening of the set screw 116 into threads 98 will push the rotation pin 104 downwardly causing the rod engagement surface 108a at the lower end of the rotation element 102 to forcibly engage the existing rod 42. The force against the existing rod 42 also causes the first portion 66 and thereby the ball insert 80 to move downwardly relative to second portion 68 forcing the outer spherical surface 82 of ball insert 80 tightly against interior spherical surface of socket 86 of second portion 68, thereby locking first portion 66 and second portion 68 securely together.

With rod connector 22 properly secured to existing spinal rod 42, tool 160 is detached from set screw 116 and removed from rod connector introducer 21. Spinal implant extension assembly 18, rod connector introducer 21 and access port 20 are also then removed from the patient. To facilitate removal of rod connector introducer 21 from rod connector 22, handle 118 may be adjustably moved to a position generally parallel to the longitudinal axis of outer sleeve 124 as shown, for example in FIG. 9. With the removal of the instruments the inline ipsilateral extension of the existing spinal construct 12 by additional spinal construct 14 as shown in FIG. 2 is complete and the incisions 144 and 146 maybe appropriately sutured. In the percutaneous procedure described, the rod connector 22 is inserted through the access port 20 and rotated for attachment to the existing rod 42 in a top loading procedure without disturbing the existing implants 34 and 36 or the previous connections to the existing rod 42. Such top loading allows a surgeon to insert the rod connector 22 by manipulating the rod connector by rotation and connect it to the existing rod 42 from above the spine facilitating the percutaneous procedure.

Figure 24:
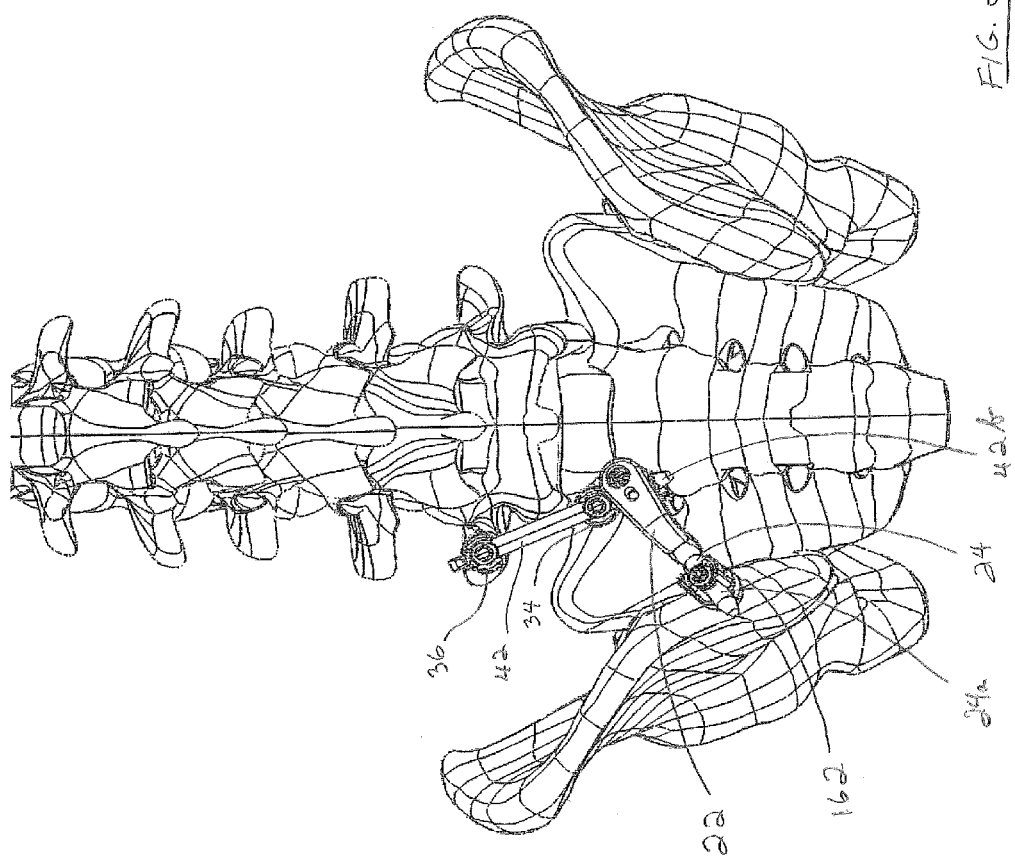
FIG. 24 is a posterior view of a portion of the patient's spine showing an additional construct extending an existing spinal construct to a further bony segment, such as the ilium.

In the procedure just described, rod connector 22 is attached to existing spinal rod 42 by targeting the interconnecting extent 42a between two existing bone engaging implants 34 and 36, each of which is engaged respectively to a corresponding vertebra 38 and 40. The elongate additional rod 24 projecting from rod connector 22 may be attached to additional spinal implant 26 in either the caudal or cephalad direction. Using the same technique described herein, it should be understood that rod connector 22 may also be used to attach an existing spinal construct to other bony segments, not only within the spine, such as vertebral bodies or the sacrum, but outside the spine, such as the ilium. Such an arrangement is contemplated, for example as shown in FIG. 24 where bone engaging implant 36 is attached to vertebral body L5 and bone engaging implant 34 is attached to segment S1 of the sacrum and these implants are interconnected by existing spinal rod 42 with extending portion 42b projecting in the caudal direction. With extending portion 42b having sufficient extent, extending portion 42b may be targeted for receipt of and connection to rod connector 22, as described above. A third bone engaging implant 162 such as an iliac screw similar to spinal implant 26 may be percutaneously secured to the ilium through a separate spaced incision with a releasable bone implant extension assembly similar to spinal implant extension assembly 18, as described in the '437 patent. Rod connector 22 may then be inserted with additional rod 24 passed subcutaneously from existing rod 42 to the iliac screw 162 in a manner as described hereinabove to form the additional construct extending from segment S1 of the sacrum to the ilium. Rod connector 22 may be configured with or without jog 72 and curved if desired to accommodate the anatomical conditions.

Figure 25:
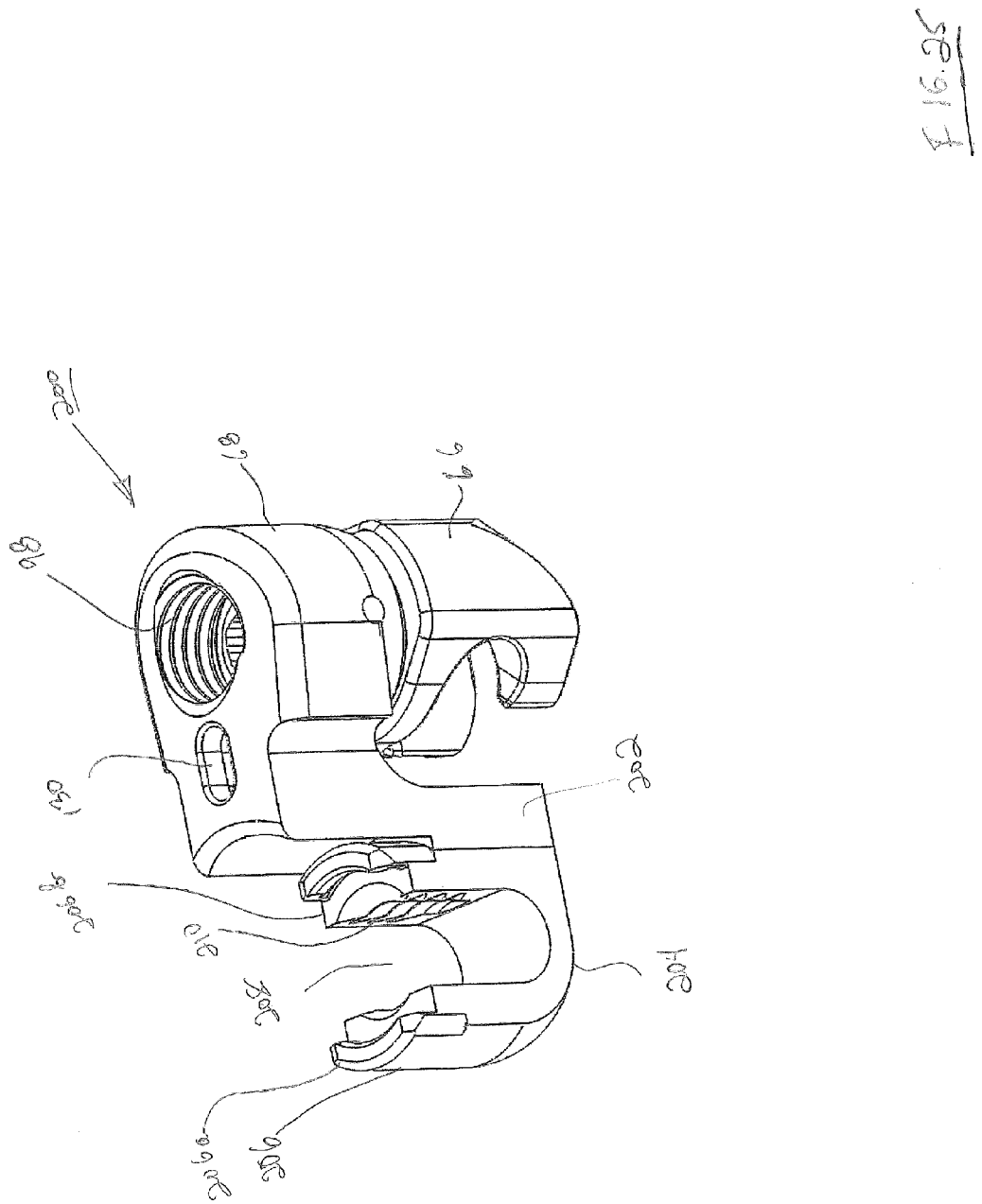
FIG. 25 is a top perspective view of a first alternative arrangement of a rod connector for attachment to an existing spinal rod of an existing spinal construct of FIG. 1.
Figure 26:
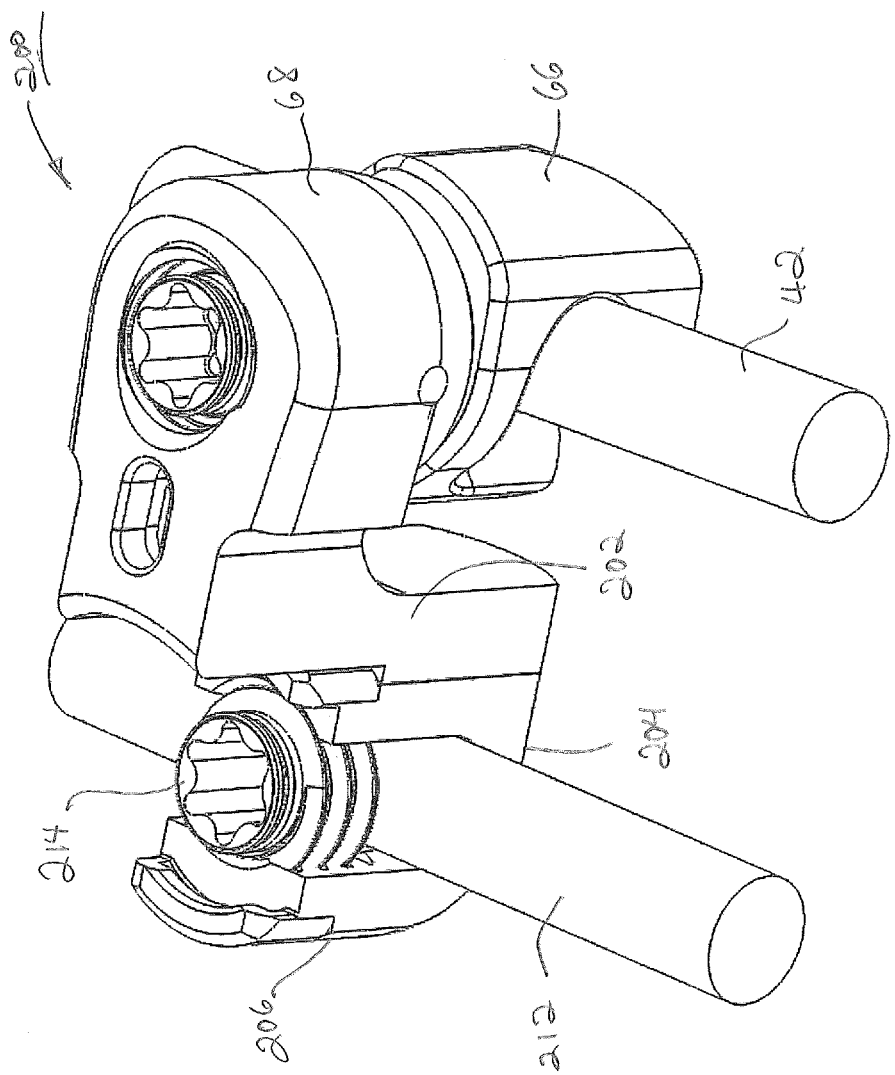
FIG. 26 is a further view of the first alternative rod connector of FIG. 25 showing an offset parallel connection of an additional rod to an existing spinal rod.

Having described a particular arrangement of rod connector 22 wherein additional rod 24 is integrally attached thereto, two alternative arrangements are described wherein a rod connector is configured to receive an additional rod rather than such additional rod being integrally attached. The first alternative arrangement is shown and described with reference to FIGS. 25 and 26. Rod connector 200 comprises a first portion 66 articulatingly attached to a second portion 68, first portion 66 and second portion 68 having structure identical to first and second portions 66 and 68 respectively of rod connector 22. Rod connector 200 further includes a connecting portion 202 projecting outwardly from second portion 68 and terminating in an additional rod support 204. Support 204 comprises a yoke 206 having a pair of opposing upstanding arms 206a and 206b defining an open ended slot 208 having internal threads 210. The slot 208 is sized and configured to receive and support therein an additional spinal rod 212 which is fastened to the yoke 206 by a set screw 214 or other suitable fastener. As shown in FIG. 26, rod connector 200 is configured to be attached to the existing spinal rod, such as rod 42 and to receive and support additional rod 212 in an orientation that may be generally parallel to existing rod 42. As such, the axis of additional rod 212 is laterally offset with respect to the axis of existing rod 42. It should be appreciated that depending upon the anatomy of the patient the orientation of the additional rod 212 relative to the existing rod 42 may not necessarily be parallel.

Figure 27:
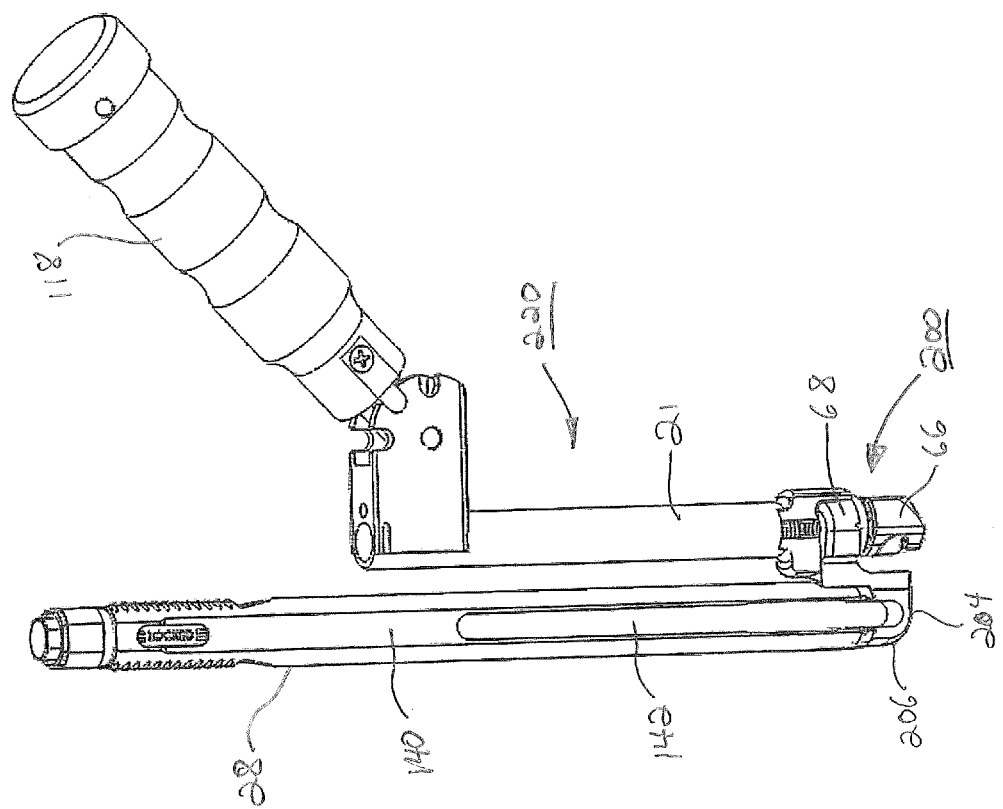
FIG. 27 is a top perspective view of the first alternative rod connector of FIG. 25 in assembly with a rod connector introducer and an additional elongate extension.

By reference to FIGS. 27 and 28 a minimally invasive technique for attaching rod connector 200 to a spinal rod in an existing spinal construct is described. A rod connector introducer 21 as described above may be releasably attached to second portion 68 of rod connector 200. An elongate extension 28 as described above with respect to spinal implant extension assembly 18 includes a hollow sleeve 140 that is releasably secured to the additional rod support 204 in the same manner as attached to additional spinal implant 26. To attach rod connector 200 to existing spinal rod such as rod 42, either the interconnecting portion 42a between two existing bone implants or the extending portion 42b projecting beyond one of the two existing bone implants may be targeted for attachment. FIG. 28 illustrates the targeting of the interconnecting portion 42a for connection. Using fluoroscopy or other suitable imaging techniques as described above, a small incision 216 is initially formed through the skin S. The incision 216 is enlarged radially and laterally with a series of sequentially increasing dilating instruments with the ultimate insertion of an oval access port 218. Oval access port 218 is sized and configured to receive the assembly 220 comprising rod connector 200, rod connector introducer 21 and the elongate extension 28. A hook rotator, such as hook rotator 136, may be inserted through rod connector introducer 21 to engage the rotation element 104 in rod connector 200 so as to restrain the hooks 74 and 76 from rotation, as set forth above. The assembly 220 is introduced into oval access port 216 with the rod connector 200 in an orientation that is maintained beneath the skin until the interconnecting portion 42a of existing spinal rod 42 is received within the opening 78 between hooks 74 and 76, as described above. Rotation of the hooks 74 and 76 about axis of engagement 100 and connection of the rod connector 200 to the interconnecting portion 42a of existing rod 42 proceeds thereafter as described above.

In the attachment of rod connector 200 by the procedure shown in FIG. 28, the yoke 206 and therefore the additional rod 212 are located laterally farther away from the midline of the patient than the existing spinal rod 42. In a variation, the rod connector 200 may be attached with the yoke 206 located interiorly of the existing spinal construct 12 such that the additional rod 212 lies closer to the midline of the patient. Once the rod connector 200 is properly secured to the existing rod 42, the rod connector introducer 21 with the hook rotator 136 and access port 218 are removed and the elongate extension 28 is maintained. A third bone engaging implant such as an iliac screw similar to spinal implant 162 in FIG. 24 may be percutaneously secured to the ilium through a separate spaced incision with a releasable bone implant extension assembly similar to spinal implant extension assembly 18, as described in the '437 patent. An additional rod may now be used to percutaneously interconnect yoke 206 of rod connector 200 with the third bone engaging implant by passing the additional rod subcutaneously beneath the skin of the patient using the extensions attached to yoke 206 and the third bone implant as guides in a manner as fully described in the '437 patent. It should be appreciated that an additional rod may also be percutaneously placed between the yoke 206 of rod connector 200 and other bony segments within the spine, such as vertebral bodies or the sacrum, either in a caudal or cephalad direction.

Turning now to FIGS. 29 and 30 the second alternative arrangement is shown and described. Rod connector 300 comprises a first portion 66 articulatingly attached to a second portion 68, first portion 66 and second portion 68 having structure identical to first and second portions 66 and 68 respectively of rod connector 22. Rod connector 300 further includes a connecting portion 302 projecting outwardly from second portion 68 and terminating in an additional rod support 304. Support 304 comprises a yoke 306 having a pair of opposing upstanding arms 306a and 306b defining an open ended slot 308 having internal threads 310. The slot 308 is sized and configured to receive and support therein an additional spinal rod 312 which is fastened to the yoke 306 by a set screw 314 or other suitable fastener. As shown in FIG. 30, rod connector 300 is configured to be attached to the existing spinal rod, such as rod 42 and to receive and support additional rod 312 in an orientation generally inline with existing rod 42. As such, the axis of additional rod 312 is generally parallel to and colinear with the axis of existing rod 42. Such an arrangement is contemplated where an existing spinal construct exists, for example, between bone implants attached to vertebral bodies L4 and L5 and extension is desired generally inline to sacral segment, S1 in the caudad direction or to vertebral body L3 in the opposite cephalad direction. In either case, the extending portion 42b of the existing rod 42 is targeted for connection by the rod connector 300. It should be appreciated that depending upon the anatomy of the patient the orientation of the additional rod 312 relative to the existing rod 42 may not necessarily be precisely inline and colinear.

To attach rod connector 300 to existing spinal rod such as rod 42 that interconnects two existing bone engaging implants, the extending portion 42b projecting beyond one of the two existing bone implants is targeted. The attachment of rod connector 300 through an oval access port such as access port 218 within dilated incision similar to incision 216, proceeds in a similar manner as described with respect to rod connector 200. A third bone engaging implant such as a pedicle screw similar to spinal implant 26, may be percutaneously secured to the sacrum or additional vertebral body through a separate spaced incision approximately 10-30 mm in length with a releasable bone implant extension assembly similar to spinal implant extension assembly 18, as described in the '437 patent. An additional rod may now be used to percutaneously interconnect yoke 306 of rod connector 300 with the third bone engaging implant by passing the additional rod subcutaneously beneath the skin of the patient using the extensions attached to yoke 306 and the third bone implant as guides in a manner as fully described in the '437 patent.

While the existing spinal construct 12 has been described herein as being extended by a single level, it should be appreciated that the extension may comprise two or more levels with the devices and instruments as described herein. In addition, while the devices and instruments described herein provide surgeons the ability to extend existing spinal constructs at least minimally invasively and more preferably, percutaneously, it should be understood that a surgeon may also use the described devices and instruments in an open procedure if that is the surgeon's surgical preference.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A rod connector for attachment to a spinal rod in an existing spinal construct implanted in a patient, comprising:
    a first portion configured to attach to said existing spinal rod upon rotation comprising a pair of spaced hooks each including a projecting rod engagement member that engages said existing spinal rod upon rotation of said first portion relative to said existing spinal rod about an axis of engagement;
    a second portion attached to said first portion in a first unlocked position in which said second portion articulates relative to said first portion and in a second locked position in which said second portion is fixed relative to said first portion, said second portion including a connecting portion projecting therefrom and having an opening extending therethrough; and
    a rotation element movably supported within said opening by a biasing element on said first portion and rotatable independently of said second portion, said rotation element engaging said first portion for jointly rotating said first portion with said spaced hooks relative to said second portion while said first portion and said second portion are in said first unlocked position.

2. The rod connector of claim 1, wherein said first portion and said second portion are coupled for articulation by a ball and socket structure.

3. The rod connector of claim 1, wherein said rotation element comprises a first end having a surface for engagement with said existing spinal rod and a second opposite end having a configuration accessible through said opening for engagement with an instrument for rotation of said rotation element to thereby cause said first portion including said hooks to rotate relative to said second portion.

4. The rod connector of claim 3, wherein said hooks define an opening for receipt of said existing spinal rod and wherein said surface at said first end of said rotation element movably projects into said opening to engage said existing rod.

5. The rod connector of claim 4, wherein said biasing element comprises a spring element normally biasing said first end of said rotation element into said opening.

6. The rod connector of claim 5, further comprising a rotatable locking element supported by said second portion and upon rotation thereof locking said first portion and said second portion in said second locked position.

7. The rod connector of claim 6, wherein said rotatable locking element includes a distal end configured to engage the second opposite end of said rotation element forcing the first end of said rotation element against said existing spinal rod to cause portions of said first and second portions of said rod connector to be drawn together in said second locked position.

8. The rod connector of claim 1, wherein said connecting portion of said second portion comprises an elongate additional rod projecting integrally therefrom and terminating in a free distal end.

9. The rod connector of claim 8, wherein said elongate additional spinal rod defines a first axis, wherein said second portion of said rod connector is attached to said first portion of said rod connector along a second axis that is transverse to said first axis, and wherein said first and second portions articulate relatively about said second axis.

10. The rod connector of claim 9, wherein said elongate additional rod comprises a jog between the distal free end and said second portion.

11. The rod connector of claim 10, wherein said second portion is disposed in substantial axial alignment with said first portion and is configured such that said elongate additional rod extends generally parallel to and collinear with said existing spinal rod.

12. The rod connector of claim 1, wherein said connecting portion is configured to receive and support an additional spinal rod.

13. A rod connector for attachment to a spinal rod in an existing spinal construct implanted in a patient, comprising:
   a first portion configured to attach to said existing spinal rod upon rotation comprising a pair of spaced hooks each including a projecting rod engagement member that engages said existing spinal rod upon rotation of said first portion relative to said existing spinal rod about an axis of engagement;
   a second portion attached to said first portion in a first unlocked position in which said second portion articulates relative to said first portion and in a second locked position in which said second portion is fixed relative to said first portion, said second portion including a connecting portion projecting therefrom and having an opening extending therethrough, wherein said connecting portion of said rod connector comprises a pair of opposed upstanding arms defining a slot therethrough for receipt and support of said additional spinal rod; and
   a rotation element supported within said opening and rotatable independently of said second portion, said rotation element engaging said first portion for jointly rotating said first portion with said spaced hooks relative to said second portion while said first portion and said second portion are in said first unlocked position.

14. The rod connector of claim 13, wherein said connecting portion is disposed with said slot defined by said upstanding arms being offset relative to said second portion and oriented to support said additional spinal rod on either lateral side of and generally parallel to said existing spinal rod.

15. The rod connector of claim 13, wherein said connecting portion is disposed with said slot defined by said upstanding arms being offset relative to said second portion and oriented to support said additional spinal rod generally parallel to and colinear with said existing spinal rod.

* * * * *